United States Patent
Raju et al.

(10) Patent No.: US 9,579,125 B2
(45) Date of Patent: Feb. 28, 2017

(54) BONE SCREW

(71) Applicant: VertiScrew, LLC, Dover, DE (US)

(72) Inventors: Muralidhara Rudhra Raju, Fountain Valley, CA (US); Amir Ali Akhavi, Irvine, CA (US); Moti Altarac, Irvine, CA (US); Joey Reglos, Lake Forest, CA (US)

(73) Assignee: VERTISCREW, LLC, Dover, DE (US)

( * ) Notice: Subject to any disclaimer, the term of this patent is extended or adjusted under 35 U.S.C. 154(b) by 0 days.

(21) Appl. No.: 14/940,034

(22) Filed: Nov. 12, 2015

(65) Prior Publication Data

US 2016/0066958 A1    Mar. 10, 2016

Related U.S. Application Data

(63) Continuation-in-part of application No. 14/175,058, filed on Feb. 7, 2014, now Pat. No. 9,451,991, which
(Continued)

(51) Int. Cl.
| | |
|---|---|
| *A61B 17/70* | (2006.01) |
| *A61B 17/88* | (2006.01) |
| *A61B 17/86* | (2006.01) |

(52) U.S. Cl.
CPC ...... *A61B 17/7035* (2013.01); *A61B 17/7037* (2013.01); *A61B 17/7085* (2013.01);
(Continued)

(58) Field of Classification Search
CPC . A61B 17/70; A61B 17/7001; A61B 17/7032; A61B 17/7034; A61B 17/7035;
(Continued)

(56) References Cited

U.S. PATENT DOCUMENTS

| | | |
|---|---|---|
| 7,588,593 B2 | 9/2009 | Aferzon |
| 7,635,380 B2 | 12/2009 | Zucherman et al. |
| | (Continued) | |

OTHER PUBLICATIONS

Biomet. Lineum OCT Spine System. Printed Apr. 4, 2014. http://www.biomet.com/wps/wcm/connect/internet/2d66d094-1a55-40fb-8fec-6e84929ad752/Lineum+OCT+Spine+System+Surgical+Technique.pdf?MOD=AJPERES&CACHEID=2d66d094-1a55-40fb-8fec-6e84929ad752 44 pages.
(Continued)

*Primary Examiner* — Lynnsy Summitt
(74) *Attorney, Agent, or Firm* — Rimas Lukas

(57) ABSTRACT

A bone fixation system with variable z-axis translation is provided. The system includes an outer tulip coupled to a bone fastener via a screw retainer. An inner tulip is coupled to the outer tulip such that the inner tulip is longitudinally movably relative to the outer tulip. The inner tulip includes a lock that provides a seat for a connecting rod. The inner tulip together with a seated rod is permitted to translate along the z-axis inside the outer tulip when in an unlocked position. Also in the unlocked position, the bone fastener is free to angulate relative to the outer tulip. The z-axis position of the inner tulip and rod relative to the outer tulip is fixed in a locked position. Also, in the locked position, the bone fastener is locked with respect to the outer tulip. The system may be adjusted between the locked and unlocked positions by way of a set screw.

22 Claims, 24 Drawing Sheets

Related U.S. Application Data is a continuation-in-part of application No. 14/175,065, filed on Feb. 7, 2014, now Pat. No. 9,463,047.

(60) Provisional application No. 61/762,854, filed on Feb. 9, 2013, provisional application No. 62/078,524, filed on Nov. 12, 2014.

(52) U.S. Cl.
CPC ...... *A61B 17/7086* (2013.01); *A61B 17/7091* (2013.01); *A61B 17/862* (2013.01); *A61B 17/8883* (2013.01)

(58) Field of Classification Search
CPC ............ A61B 17/7037; A61B 17/7038; A61B 17/7041; A61B 17/7046
See application file for complete search history.

(56) References Cited

U.S. PATENT DOCUMENTS

| | | | | |
|---|---|---|---|---|
| 7,828,829 B2* | 11/2010 | Ensign | ............... | A61B 17/7032 606/287 |
| 7,862,588 B2* | 1/2011 | Abdou | ............... | A61B 17/8685 606/246 |
| 8,100,947 B2* | 1/2012 | Ensign | ............... | A61B 17/7032 606/267 |
| 8,123,782 B2 | 2/2012 | Altarac et al. | | |
| 8,221,472 B2* | 7/2012 | Peterson | ............ | A61B 17/7032 606/266 |
| 8,236,035 B1* | 8/2012 | Bedor | ................ | A61B 17/7037 606/266 |
| 8,308,782 B2* | 11/2012 | Jackson | ............. | A61B 17/7008 606/305 |
| 8,361,123 B2* | 1/2013 | Fanger | ............... | A61B 17/7037 606/270 |
| 9,439,700 B2* | 9/2016 | Peterson | ............ | A61B 17/7032 |
| 2010/0249846 A1 | 9/2010 | Simonson | | |
| 2010/0305620 A1* | 12/2010 | Gotfried | ............ | A61B 17/6466 606/305 |
| 2011/0112578 A1 | 5/2011 | Keiser et al. | | |
| 2012/0016425 A1 | 1/2012 | Shaffrey et al. | | |
| 2014/0358182 A1* | 12/2014 | Puekert | .............. | A61B 17/7037 606/264 |
| 2015/0196338 A1* | 7/2015 | Biedermann | ...... | A61B 17/7037 606/305 |

OTHER PUBLICATIONS

Scoliosisnutty.com. Medtronic TSRH-3D system. Printed Apr. 4, 2014. http://www.scoliosisnutty.com/tsrh.php 2 pages.

* cited by examiner

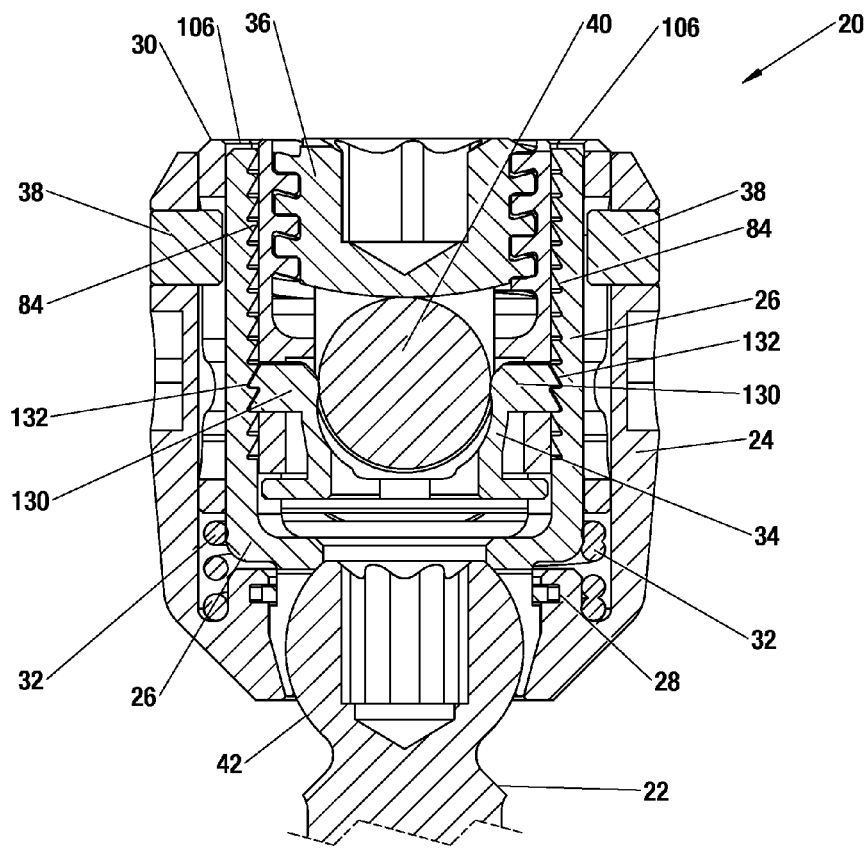
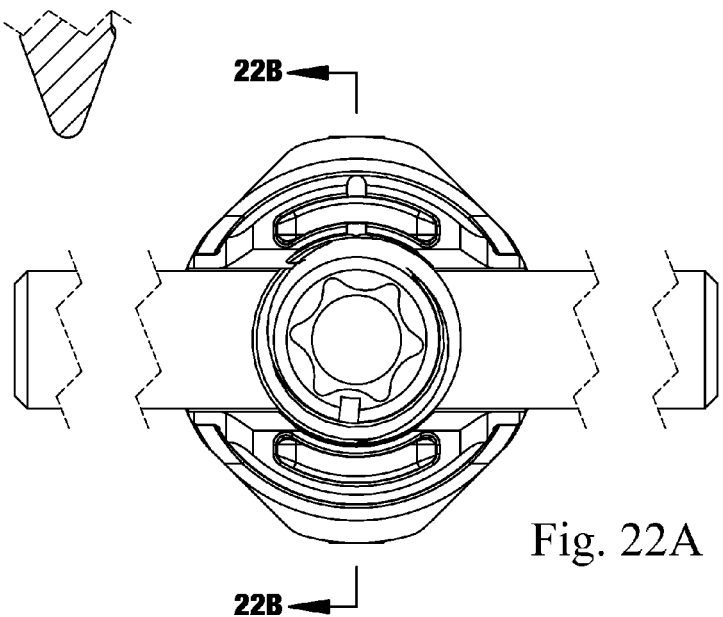
Fig. 22B
Fig. 22A

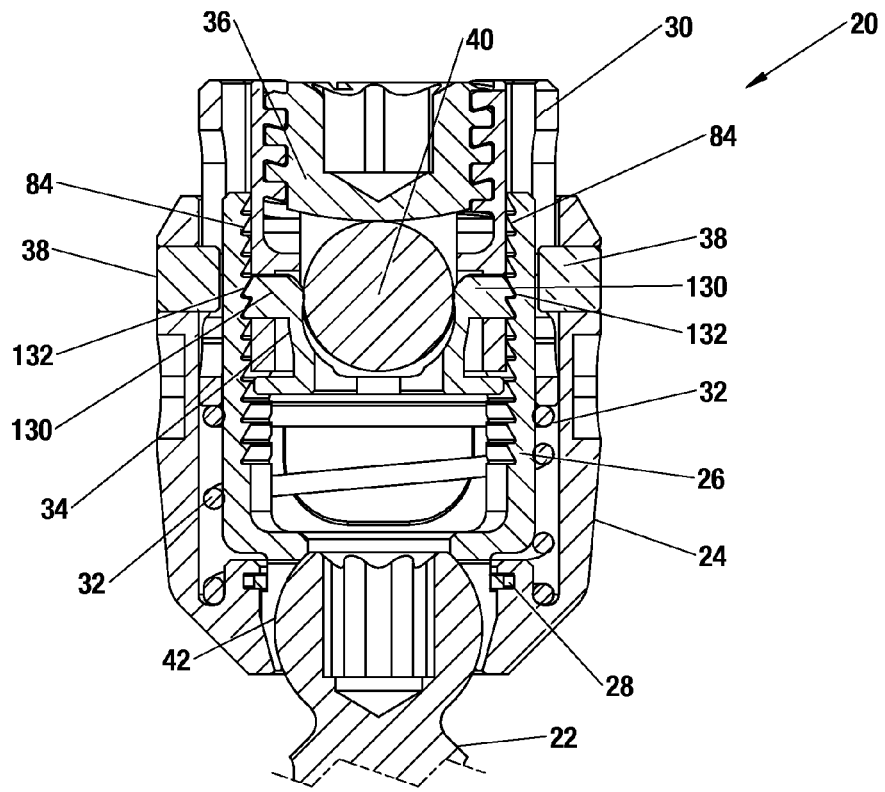
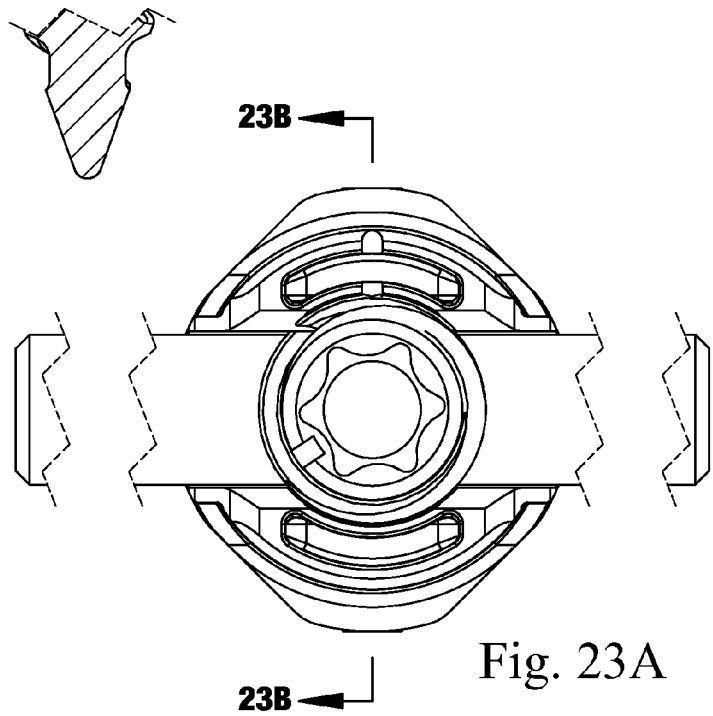
Fig. 23B
Fig. 23A

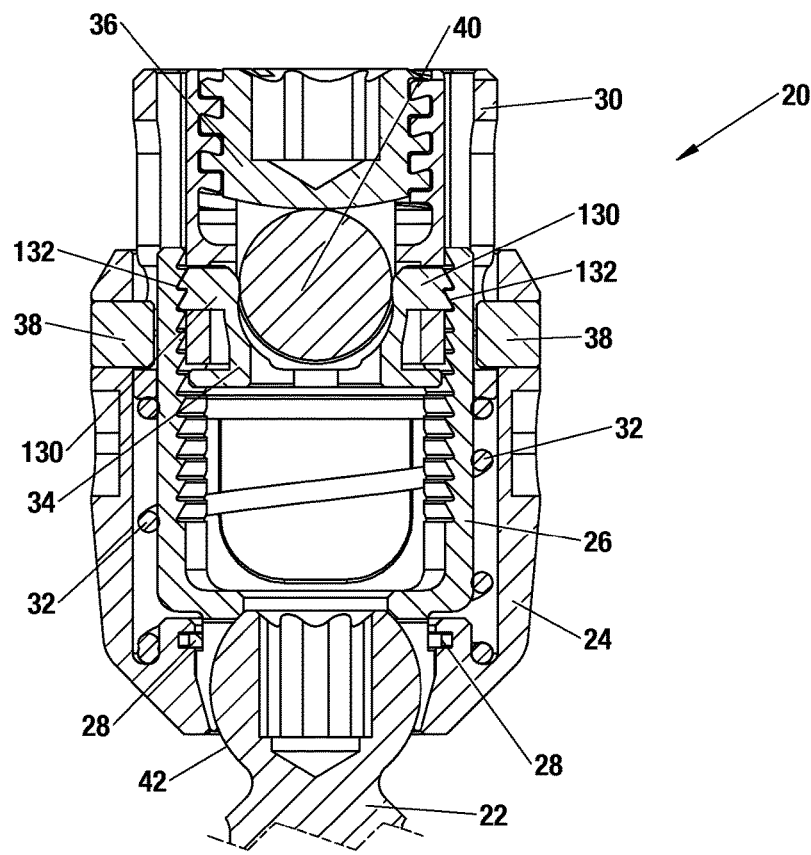
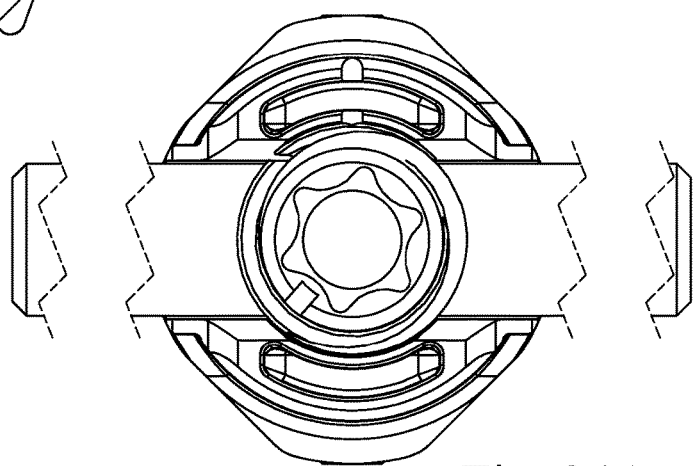
Fig. 24B
Fig. 24A

BONE SCREW

CROSS-REFERENCE TO RELATED APPLICATIONS

This application claims priority to and benefit of U.S. Provisional Patent Application Ser. No. 62/078,524 entitled "Bone screw" filed on Nov. 12, 2014 incorporated by reference in its entirety herein, and this application is a continuation-in-part of U.S. patent application Ser. No. 14/175,058 entitled "Bone screw" filed on Feb. 7, 2014 incorporated by reference in its entirety herein and a continuation-in-part of U.S. patent application Ser. No. 14/175,065 entitled "Bone screw" filed on Feb. 7, 2014 incorporated by reference in its entirety herein, both of which claim priority to and benefit of U.S. Provisional Patent Application Ser. No. 61/762,854 entitled "Threaded bone screw with variable Z-axis translation" filed on Feb. 9, 2013 incorporated by reference in its entirety herein.

FIELD OF THE INVENTION

The present invention is directed to surgical devices and methods, and in particular, to bone fixation devices used in spinal surgery.

BACKGROUND OF THE INVENTION

Spinal fusion is a common surgical procedure used to correct numerous disease states including degenerative disorders, trauma, instability, and deformity. A frequent method of fusion entails the use of bone screws placed through various sections of the vertebral body including the body, pedicle, facets, lamina, lateral masses, and/or transverse processes. These screws are then linked rigidly with a rod, plate or other fixation device to immobilize the vertebral segments.

Due to the variation in a patient's anatomy and differences in screw placement technique, screws are often not perfectly aligned which makes securement of a fixation device more difficult. To solve this, many screws that have a threaded shank portion incorporate an articulating tulip or receiver connected to the proximal end of the shank portion, such as in a polyaxial or multi-axial bone screw. Polyaxial bone screws allow for a variation in the angulation of the tulip/receiver relative to the shank portion in order to allow the tulip/receiver to more closely align for receiving a fixation device such as a fixation rod within the tulip/receiver. Some bone screws allow for the lateral translation of the tulip/receiver relative to its point of fixation. Further alignment may be accomplished by contouring of the fixation device itself to compensate for any remaining misalignment. For example, if a fixation rod is employed, the rod is bent to conform to the patient anatomy and location of the tulip/receiver to securely attach thereto.

A body in three-dimensional space has six degrees of freedom, namely, translation through the perpendicular x, y, and z planes, combined with the rotation through the three perpendicular axes (pitch, yaw, and roll). Typical articulating polyaxial screws allow three dimensional rotations (pitch, yaw, and roll). Some designs also incorporate lateral x-plane translation. Longitudinal translation (y-plane), generally along the cephalad-caudal direction or axis of the fixating rod or plate, is usually accomplished by fixing the tulip/receiver to different positions along the rod or plate.

Anterior/posterior translation (along the z-plane) is typically accomplished by persuading the vertebral body itself, using instruments to raise or lower the vertebral body until the tulip/receiver is properly aligned with the rod or plate. Frequently, however, this anterior/posterior translation may not be desirable as it may produce suboptimal alignment of the vertebral bodies or even cause fractures of the bone or pullout of the shank portion of the screw from the bone due to the stresses placed on it during the persuading process. The other option for adjustment along the z-axis employed is to partially back out the screw, leaving it proud. This, however, reduces the bone-screw interface thereby weakening the overall strength of the construct. Some designs, such as the one illustrated in U.S. Pat. No. 7,588,593, allow for vertical adjustment but require manual assembly of the screw and head construct during surgery. Hence, there is a need for modular bone screw assemblies that can provide variable angle orientation together with z-axis translation which are easy to assemble.

SUMMARY OF THE INVENTION

According to one aspect of the invention, a bone fixation system is provided. The bone fixation system includes a bone fastener. The bone fastener includes bone engaging portion and a head connected to the bone engaging portion. The bone fixation system includes an outer receiver having a proximal end, a distal end and a longitudinal axis. The outer receiver includes a sidewall extending between the proximal end and the distal end and having an inner surface and an outer surface. An inner bore extends through the outer receiver between a top opening at the proximal end and a bottom opening at the distal end. The outer receiver includes two oppositely disposed arms defined by the sidewall. At least one rod channel is defined between the two arms. The at least one rod channel is interconnected with the top opening and the inner bore. A hole is provided in each arm that extends from the inner surface to the outer surface. The bone fixation system includes a screw retainer sized to fit inside the outer receiver. The screw retainer includes two oppositely disposed arms connected to a bone fastener-receiving portion at a distal end of the screw retainer. The screw retainer includes at least one channel defined between the arms. Each arm has an interlocking inner surface. The bone fastener is coupled to the screw retainer in the bone fastener-receiving portion such that the bone faster is permitted to angulate in an unlocked configuration. The bone fixation system includes an inner receiver sized to fit inside within the outer receiver. The inner receiver includes a base and two oppositely disposed arms extending upwardly from the base. The inner receiver includes at least one channel defined between the arms. Each arm of the inner receiver has an interlocking inner surface. Each arm of the inner receiver includes a passageway having an opening at the proximal end of the inner receiver and extending to an opening at the distal end of the inner receiver. Each passageway is sized and configured to receive an arm of the screw retainer within the passageway. The base of the inner receiver includes a lock-receiving portion having two oppositely disposed holes extending from the inside of the inner receiver outwardly into the passageways. Each arm of the inner receiver includes a longitudinal notch extending inwardly from the outer surface of the inner receiver. The bone fixation system includes two pins sized and configured to be received within the longitudinal notches of the inner receiver and extend through the holes in the arms of the outer receiver. The inner receiver is coupled to the outer receiver with the pins such that the inner receiver is movable longitudinally relative to the outer receiver. The bone fixation system includes a lock located inside the lock-receiving portion of the inner receiver. The lock including a rod-receiving location having a reduced entryway. The rod-receiving location is sized and configured to receive a connecting rod. The lock includes two outwardly laterally extending locking prongs having distal interlocking surfaces. The locking prongs are configured to extend into the holes in the inner receiver such that the distal interlocking surfaces of the locking prongs engage the interlocking inner surfaces of the screw retainer in a locked configuration. The bone fixation system includes a spring disposed between the inner receiver and the outer receiver. The spring is configured to bias the inner receiver proximally relative to the outer receiver. The bone fixation system includes a removable set screw located between the arms of the inner receiver and having an interlocking outer surface configured to interlock with the interlocking inner surface of the arms of the inner receiver. The bone fixation system includes an elongate connecting rod removably located between the arms of the inner receiver. The bone fixation system includes an unlocked position in which the bone fastener angulates with respect to the outer receiver and the inner receiver is free to translate longitudinally with respect to the outer receiver and a locked position in which the bone fastener and inner receiver are fixed and the longitudinal position of the connecting rod is fixed with respect to the outer receiver. The locked configuration is achieved by threading the set screw downwardly within the inner receiver to move the connecting rod into the rod receiving location which causes the locking prongs to extend outwardly to engage the inner interlocking surface of the screw retainer and simultaneously to move the screw retainer downwardly onto the bone fastener to lock the angulation of the bone fastener relative to the outer receiver.

According to another aspect of the invention, a bone fixation system is provided. The bone fixation system includes an inner receiver nested within an outer receiver. The bone fixation system includes a connecting rod connected to the inner receiver and configured to translate in the longitudinal direction relative to the outer receiver in an unlocked configuration. The inner receiver includes two oppositely disposed elongate longitudinal notches and the outer receiver includes oppositely disposed pin holes. The inner receiver is coupled to the outer receiver with two pins inserted into the pin holes and into the longitudinal notches.

According to another aspect of the invention, a bone fixation system is provided. The bone fixation system includes an inner receiver nested within an outer receiver. The bone fixation system includes a connecting rod connected to the inner receiver and configured to translate in the longitudinal direction relative to the outer receiver in an unlocked configuration. The system further includes a screw retainer configured to couple a bone screw to the outer receiver. The screw retainer includes two arms and the inner receiver includes two passageways sized and configured to receive the two arms of the screw retainer.

According to another aspect of the invention, a bone fixation system is provided. The bone fixation system includes an inner receiver nested within an outer receiver. The bone fixation system includes a connecting rod connected to the inner receiver and configured to translate in the longitudinal direction relative to the outer receiver in an unlocked configuration. The system further includes a spring between the inner receiver and the outer receiver. The spring is configured to bias the inner receiver in the proximal direction relative to the outer receiver.

According to another aspect of the invention, a bone fixation system is provided. The bone fixation system includes an inner receiver nested within an outer receiver. The bone fixation system includes a connecting rod connected to the inner receiver and configured to translate in the longitudinal direction relative to the outer receiver in an unlocked configuration. The system further includes a screw retainer coupled to the outer receiver. The screw retainer includes two channels. The inner receiver includes two channels. The outer receiver includes two channels. All of the channels are aligned to provide a vertical longitudinal passageway for the connecting rod.

According to another aspect of the invention, a bone fixation system is provided. The bone fixation system includes an inner receiver nested within an outer receiver. A bone fastener is coupled to the outer receiver and permitted to angulate in an unlocked configuration. The bone fixation system includes a connecting rod connected to the inner receiver and configured to translate in the longitudinal direction relative to the outer receiver in the unlocked configuration. The system further includes a locked configuration in which the translation of the connecting rod and inner receiver is arrested and the angulation of the bone fastener is fixed.

According to another aspect of the invention, a bone fixation system is provided. The bone fixation system includes an inner receiver nested within an outer receiver. A bone fastener is coupled to the outer receiver and permitted to angulate in an unlocked configuration. The bone fixation system includes a connecting rod connected to the inner receiver and configured to translate in the longitudinal direction relative to the outer receiver in the unlocked configuration. The system further includes a locked configuration in which the translation of the connecting rod and inner receiver is arrested and the angulation of the bone fastener is fixed. The system further includes a lock coupled to the inner receiver and configured to receive the connecting rod. The system transitions from an unlocked configuration to a locked configuration when the connecting rod is moved into the lock.

According to another aspect of the invention, a bone fixation system is provided. The bone fixation system includes an inner receiver nested within an outer receiver. A bone fastener is coupled to the outer receiver and permitted to angulate in an unlocked configuration. The bone fixation system includes a connecting rod connected to the inner receiver and configured to translate in the longitudinal direction relative to the outer receiver in the unlocked configuration. The system further includes a locked configuration in which the translation of the connecting rod and inner receiver is arrested and the angulation of the bone fastener is fixed. The system further includes a lock coupled to the inner receiver and configured to receive the connecting rod. The system transitions from an unlocked configuration to a locked configuration when the connecting rod is moved into the lock. The system includes a screw retainer coupled to the bone fastener. The screw retainer includes interlocking inner surfaces. The lock includes outwardly extending locking prongs that engage the interlocking surfaces of the screw retainer in the locked configuration.

According to another aspect of the invention, a bone fixation system is provided. The bone fixation system includes an inner receiver nested within an outer receiver. A bone fastener is coupled to the outer receiver and permitted to angulate in an unlocked configuration. The bone fixation system includes a connecting rod connected to the inner receiver and the connecting rod and the inner receiver configured to translate together in the longitudinal direction relative to the outer receiver in the unlocked configuration.

The system further includes a locked configuration in which the translation of the connecting rod and inner receiver is arrested and the angulation of the bone fastener is fixed. The system further includes a lock coupled to the inner receiver and configured to receive the connecting rod. The system transitions from an unlocked configuration to a locked configuration when the connecting rod is moved into the lock. The system includes a screw retainer coupled to the bone fastener. The screw retainer includes interlocking inner surfaces. The lock includes outwardly extending locking prongs that engage the interlocking surfaces of the screw retainer in the locked configuration. The screw retainer translates downwardly from the unlocked configuration to a locked configuration to lock the angulation of the bone fastener.

According to another aspect of the invention, a bone fixation system is provided. The bone fixation system includes a first receiver, a second receiver and a third receiver. The second receiver is located inside the first receiver. The second receiver is coupled to the first receiver. The third receiver is coupled to the first receiver such that the third receiver is capable of longitudinal translation relative to the first receiver. The system includes a connecting rod connected to the third receiver. The system includes a locked position in which the translation of the third receiver relative to the first receiver is locked and an unlocked position in which third receiver is free to translate relative to the first receiver.

According to another aspect of the invention, a bone fixation system is provided. The bone fixation system includes a first receiver and a second receiver coupled to the first receiver such that the second receiver translates relative to the first receiver along a longitudinal axis in a locked position. The second receiver is configured to receive a connecting rod such that the connecting rod translates with the second receiver in an unlocked position. A bone fastener is connected to the distal end of the system such that the bone fastener angulates with respect to the first receiver in the unlocked position. A lock is connected to the second receiver having an unlocked position in which the bone fastener angulates with respect to the first receiver and the second receiver translates with respect to the first receiver and an locked position in which the angulation of the bone fastener and the translation of the second receiver is fixed.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary the dimensions of the various features are arbitrarily expanded or reduced for clarity. Included in the drawings are the following figures:

FIG. 22A is a top view of a bone fixation system in a locked, low-profile configuration according to the present invention.

FIG. 22B is a cross-sectional view taken along line 22-22 of FIG. 22A of a bone fixation system in a locked, low-profile configuration according to the present invention.

FIG. 23A is a top view of a bone fixation system in a locked, intermediate profile configuration according to the present invention.

FIG. 23B is a cross-sectional view taken along line 23-23 of FIG. 23A of a bone fixation system in a locked, intermediate profile configuration according to the present invention.

FIG. 24A is a top view of a bone fixation system in a locked, high-profile configuration according to the present invention.

FIG. 24B is a cross-sectional view taken along line 24-24 of FIG. 24A of a bone fixation system in a locked, high-profile configuration according to the present invention.

DETAILED DESCRIPTION OF THE INVENTION

Figure 1:
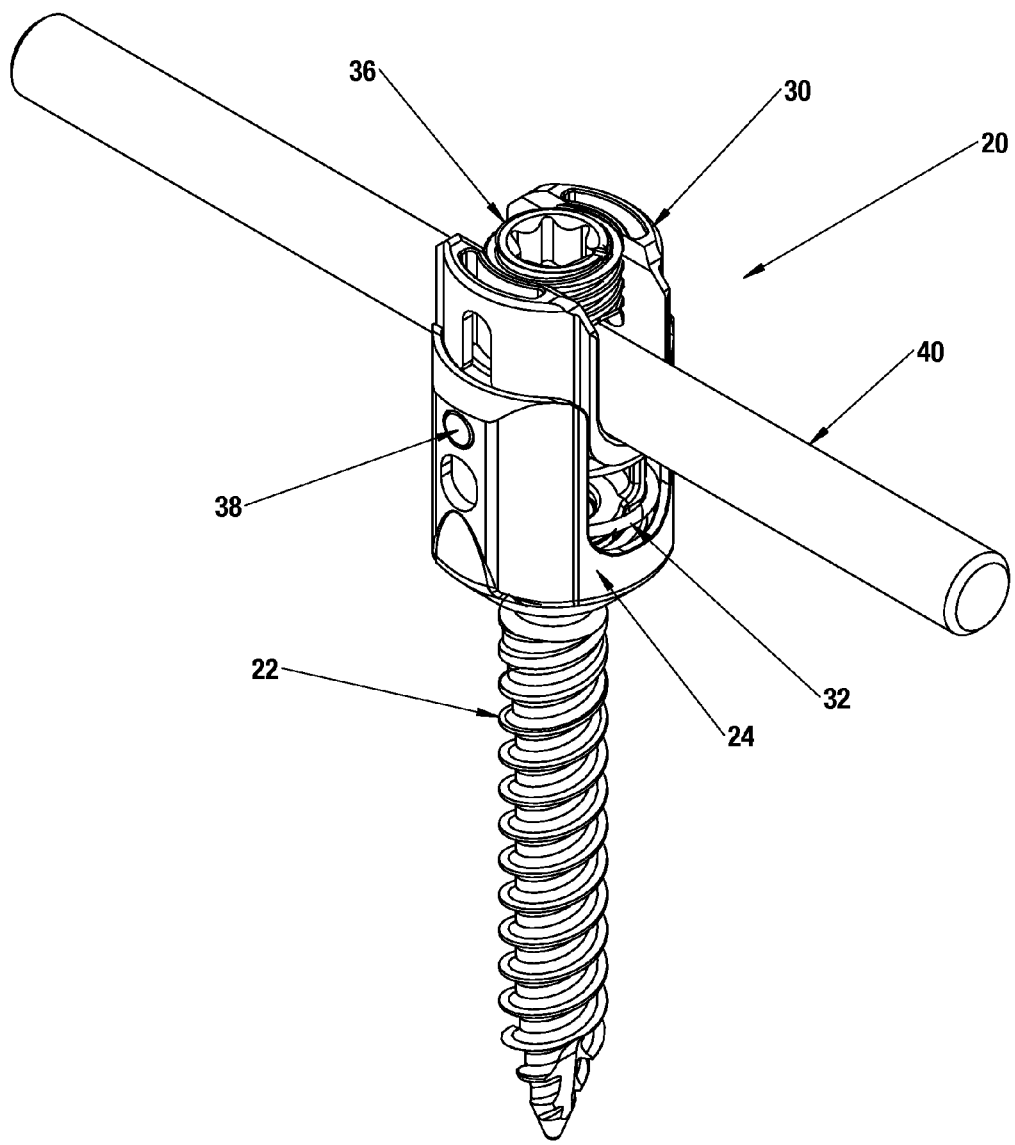
FIG. 1 is a top perspective view of a bone fixation system according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It should also be understood that the term "system", when referring to a system of the present invention, most typically refers to a set of components which includes multiple bone stabilization components such as a superior or cephalad component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intra-operatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means or fixation devices such as elongate fixation members, rods and plates but are not limited thereto. In other embodiments, components interface, in a manner that constrains their relative movement and enables the treated segment to mimic the function or partial function and/or movement or partial movement of a healthy segment. Typically, spinal interconnecting means is a dorsally positioned component, i.e., positioned posterior of the superior and inferior components, or may be a laterally positioned component, i.e., positioned to the outer side of the posterior and inferior components. The structures may include one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts. In addition, each of the inventive embodiments described herein may be employed in a percutaneous, minimally invasive surgical procedure, a mini-open procedure or an open procedure. Utilization of minimally invasive techniques can shorten the procedure's time and speed recovery by the patient. The application of these inventions in a minimally invasive manner is not a requirement. Also, the invention is not limited to the spine and may be employed in other areas where fixation to bone is useful either in human or animal applications.

Turning to FIG. 1, there is shown a bone fixation system 20 suitable for use in orthopedic surgery. In particular, the bone fixation systems in the present invention are all adapted for use in spinal fixation procedures and as such can be installed in a patient for treating at least one or more of the following: degenerative disc disease, spinal stenosis, spondylolisthesis, spinal deformities, fractures, pseudarthrosis, tumors, failed previous fusions, other vertebral segment trauma or diseases. However, the invention is not so limited and various aspects of the present invention may have application for other procedures.

Figure 2:
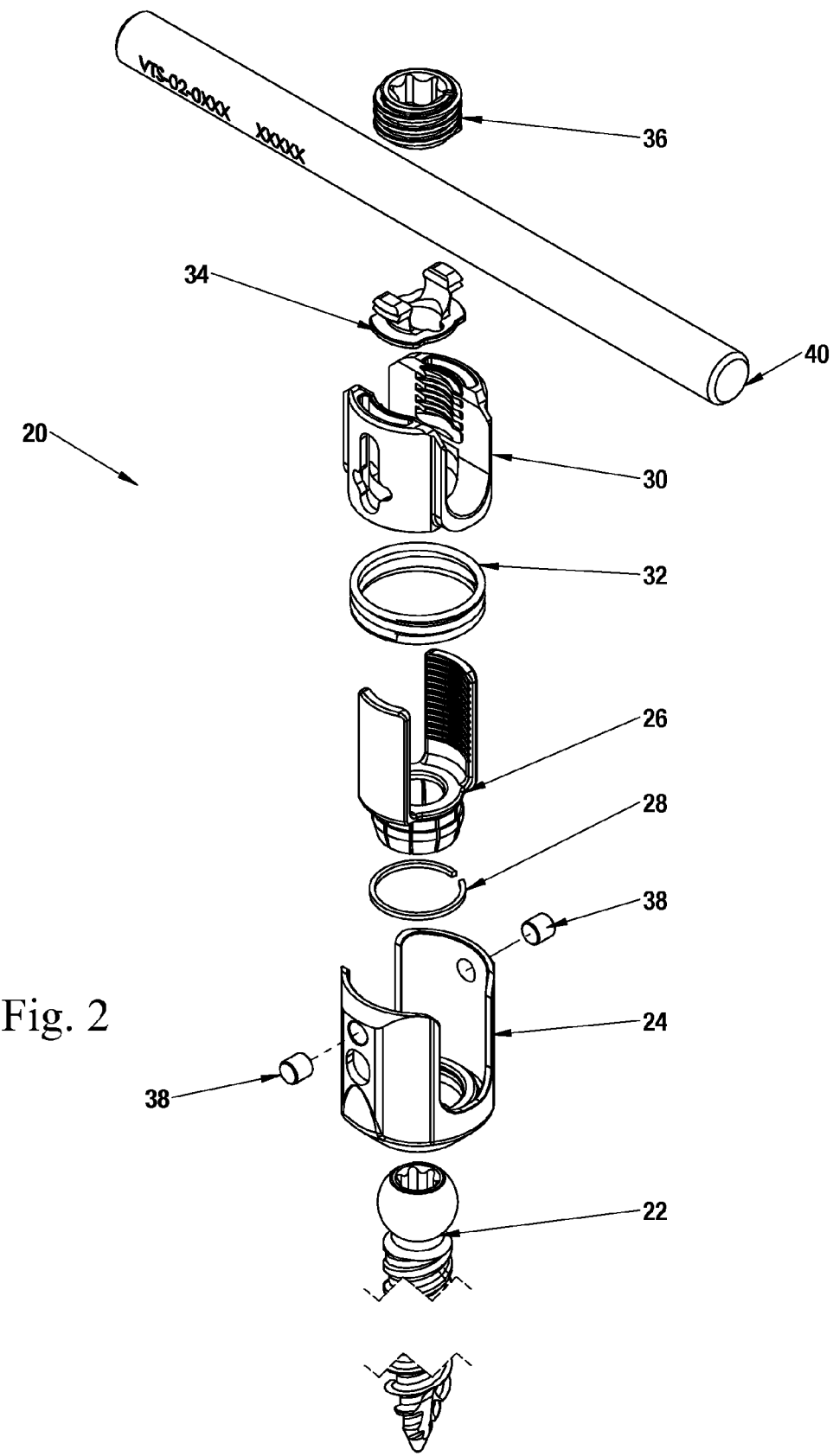
FIG. 2 is a top perspective, exploded view of a bone fixation system according to the present invention.

With reference to FIG. 1 and, in particular, to FIG. 2, the bone fixation system 20 includes a bone fastener 22, an outer receiver 24, also called an outer tulip, a screw retainer 26 coupled to the bone fastener 22 via a retaining ring 28, an inner receiver 30, also called an inner tulip, a spring 32, a lock 34, a set screw 36, and retaining pins 38. The bone fixation system 20 may also include an elongate fixation member 40 also called a connecting rod. It should be noted, however, that although the bone fixation system 20 is generally illustrated and described as a single assembly for use with a single connecting rod 40, any combination of bone fixation systems 20 and connecting rods 40 can be employed during a surgical procedure. For example, in a single level spinal fixation procedure, two bone fixation systems 20 can receive a single connecting rod 40 along one side of the spine and two bone fixation systems 20 can receive another connecting rod 40 along the opposite side of the spine. A multiple level spinal fixation procedure, however, will generally require additional bone fixation systems 20. In addition, the bone fixation systems 20 need not be coupled to adjacent vertebral bodies, but rather, the bone fixation systems 20 can be positioned so as to skip adjacent vertebral bodies if desired. The bone fixation system 20 can be composed of any suitable material, such as titanium, stainless steel, metal, metal alloys, polymers, synthetic polymers such as polyether ether ketone (PEEK), plastics or any other sufficiently rigid and strong material which is biologically compatible and can maintain its strength in vivo for at least six months. The various components of the bone fixation system 20 can be made of materials that are different from the other components of the system 20.

Figure 3:
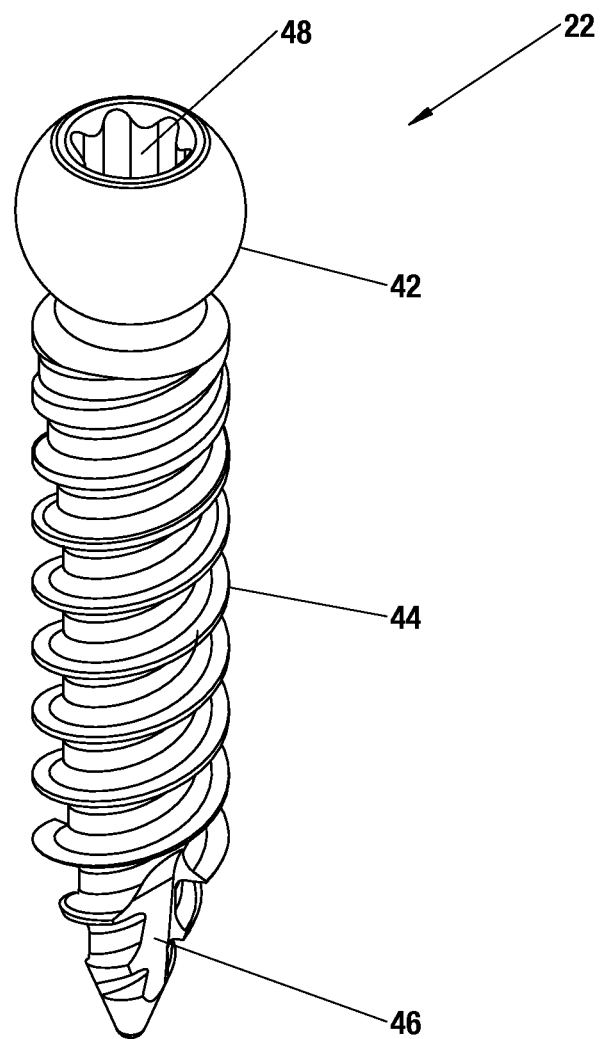
FIG. 3 is a top perspective view of a bone fastener according to the present invention.
Figure 4:
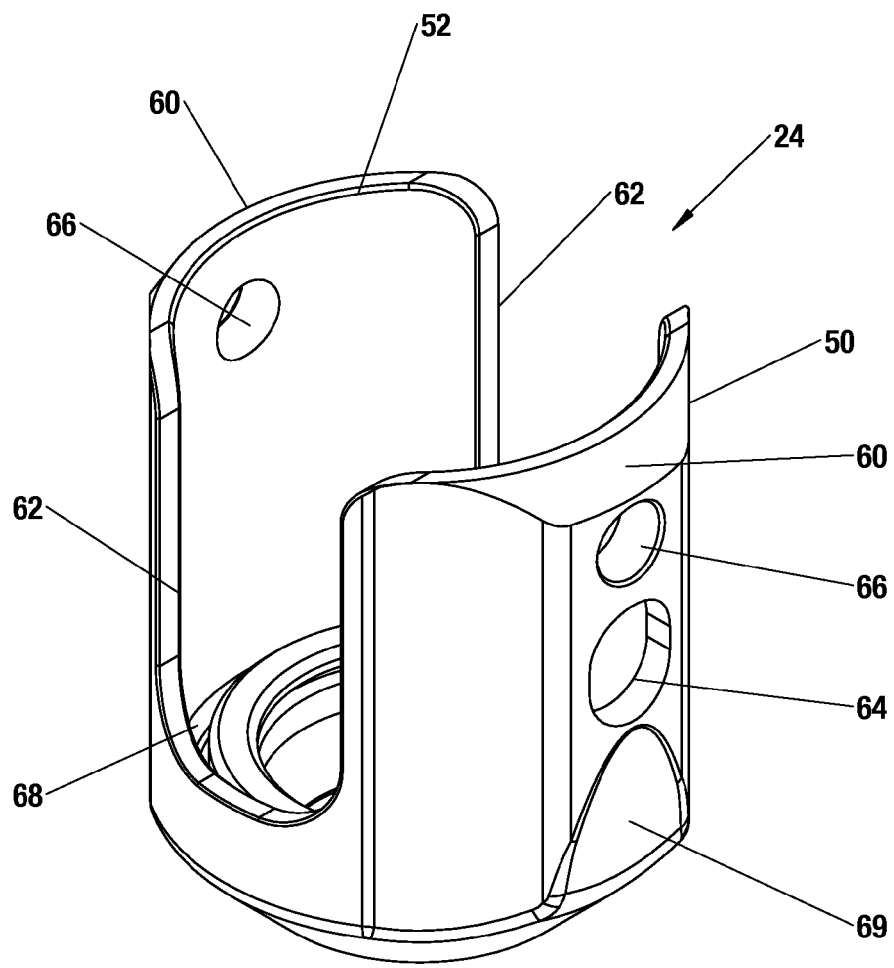
FIG. 4 is a top perspective view of an outer receiver according to the present invention.
Figure 5:
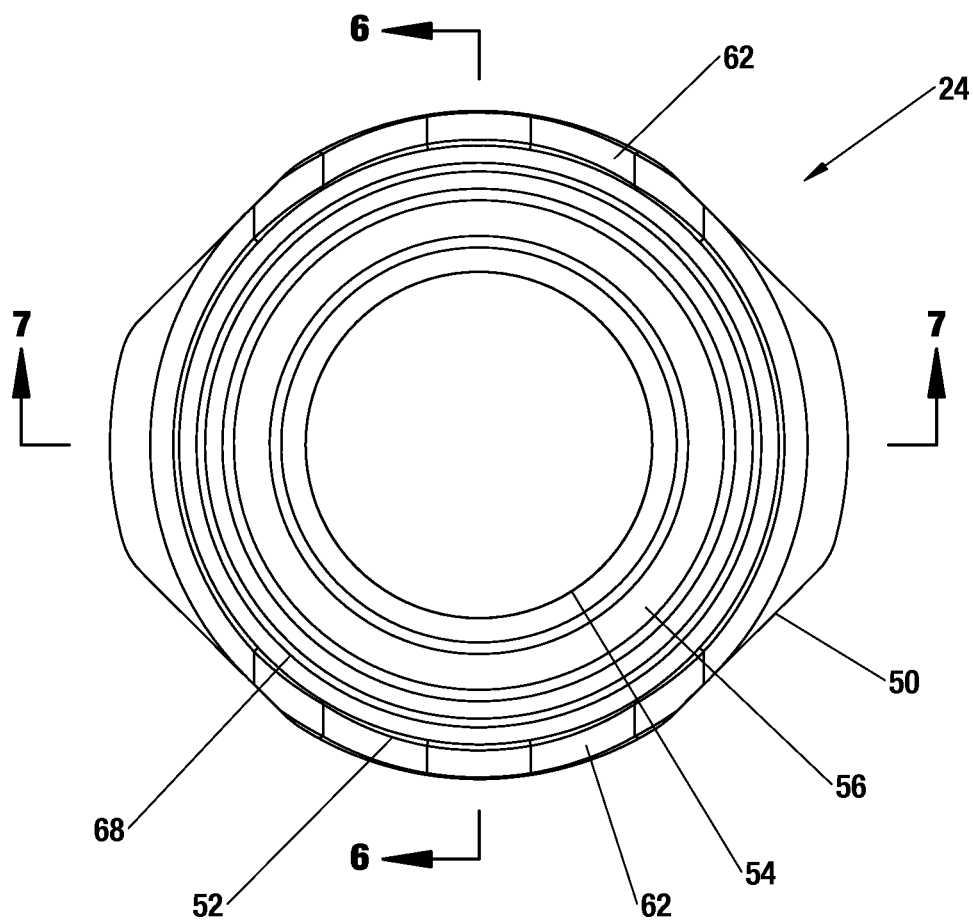
FIG. 5 is a top view of an outer receiver according to the present invention.
Figure 6:
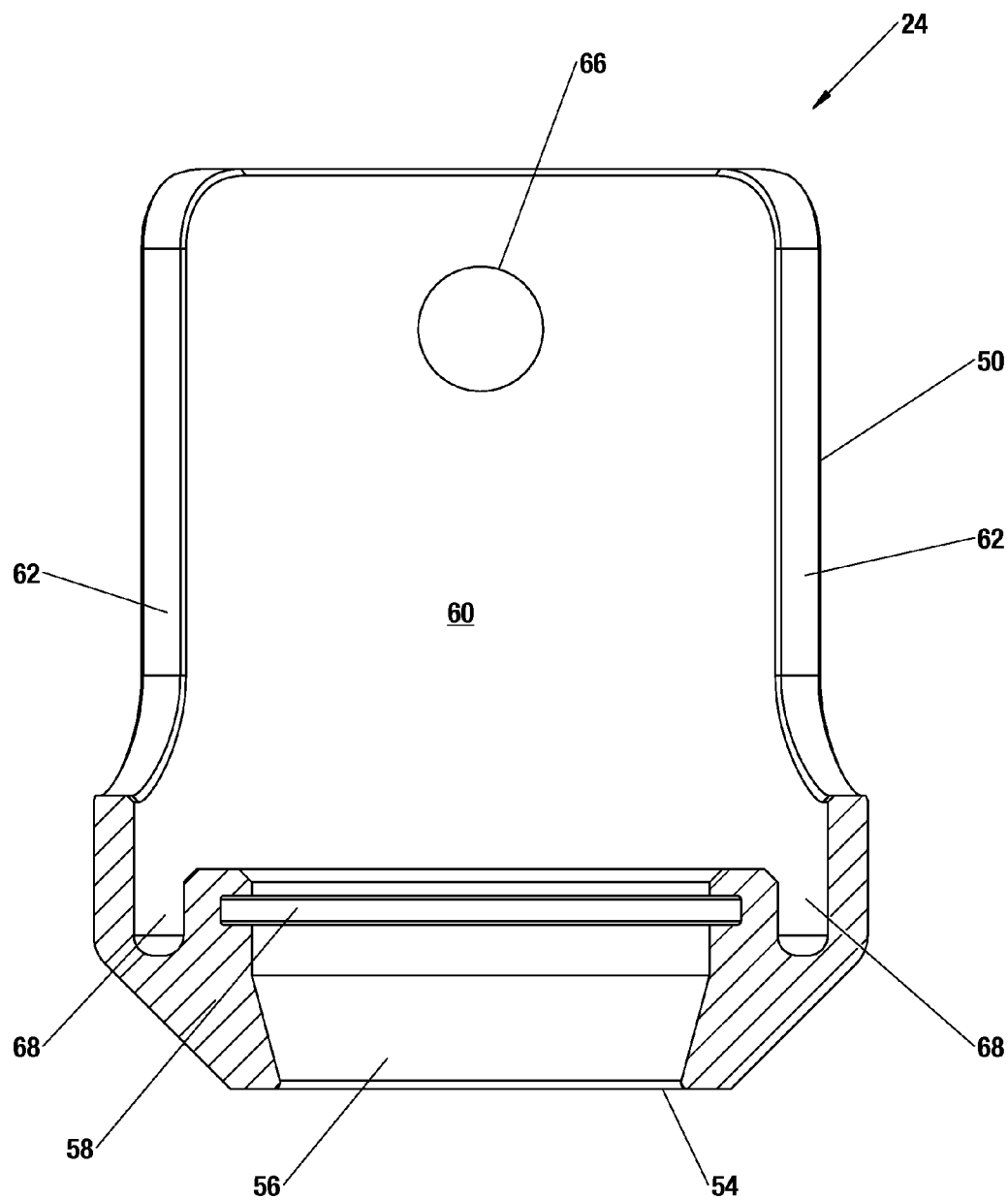
FIG. 6 is a cross-sectional view taken along line 6-6 of FIG. 5 of an outer receiver according to the present invention.
Figure 7:
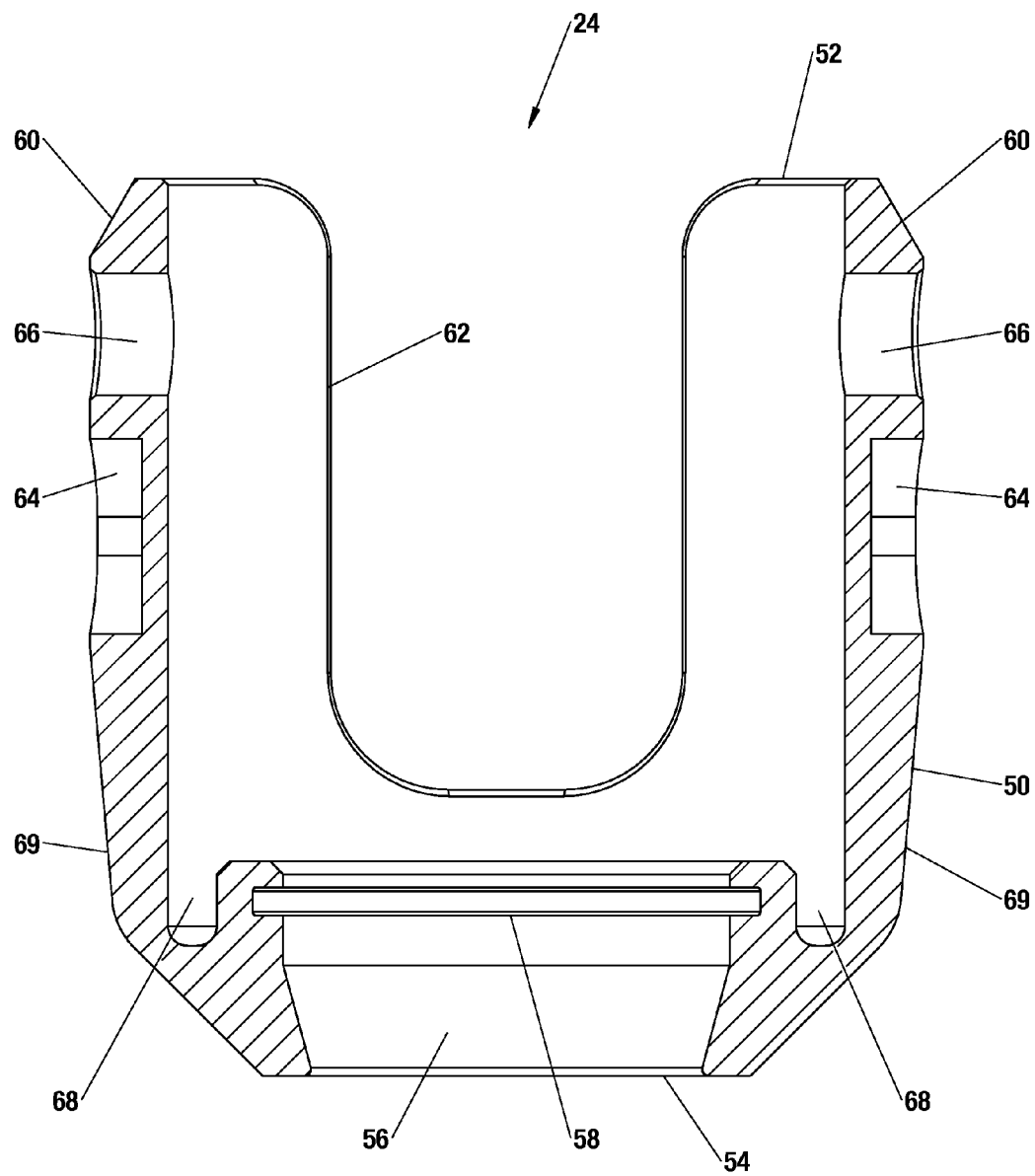
FIG. 7 is a cross-sectional view taken along line 7-7 of FIG. 5 of an outer receiver according to the present invention.

Turning now to FIG. 3, the bone fastener 22 is configured to engage the anatomy to couple the bone fixation system 20 to the anatomy. The bone fastener 22 includes a head 42 at a proximal end and an elongate threaded shank portion 44 extending between the head 42 and a distal end along a longitudinal axis. The bone fastener 22 is configured as a typical bone screw; however, the invention is not so limited and any fastener or other-shaped anchor may be employed such as a laminar hook. The bone fastener 22 may be a self-tapping bone screw having at least one cutting flute 46 and the shank portion 44 may include double threads. Alternatively, a bone screw that requires a hole to be pre-tapped prior to insertion may be employed. The head 42 can be generally arcuate having a curved or bulbous outer surface and may be spherical or partially spherical in shape. The head 42 can include a driver connection feature 48 at the proximal end for mating with any type of driver such as a hex tool having a hexagonal distal tip to enable the application of torque to drive the bone fastener 22 into the anatomy. The driver connection feature 48 shown in FIG. 3 is a daisy-shaped socket. Generally, the head 42 has a wider lateral dimension relative to the lateral dimension of the shank portion 44.

Turning now to FIGS. 4-7, the outer receiver 24 will now be described in detail. The outer receiver 24 includes a sidewall 50 having an outer surface and an inner surface. The sidewall 50 forms a proximal opening 52 at the proximal end leading into a substantially cylindrical inner bore that extends to a distal opening 54 at the distal end of the outer receiver 24. The distal opening 54 is configured for receiving at least a part of the screw retainer 26, shank portion 44 and/or head 42 of the bone fastener 22. The inner surface of the outer receiver 24 at the distal end defines a screw retainer-receiving location 56. The screw retainer-receiving location 56 include a retaining ring slot 58 sized and configured to receive the retaining ring 28. The screw retainer-receiving location 46 is contoured and forms a conforming seat for the distal end of the screw retainer 26.

Still referencing FIGS. 4-7, the sidewall 50 of the outer receiver 24 forms two upstanding, oppositely disposed arms 60. The arms 60 are spaced apart from each other to define at least one channel 62 in the sidewall 50. In one variation, the channels 62 comprise two oppositely disposed, substantially U-shaped spaces that interconnect with the proximal opening 52 and the inner bore of the outer receiver 24. The channels 62 are shaped to receive an elongate fixation member 40 such as a spinal fixation rod or other elongate member to be connected to the outer receiver 24 by placement of the elongate fixation member 40 into the channels 62. The outer surface of the outer receiver 24 may include two small recesses 64 oppositely disposed in the arms 60 for permitting an insertion instrument, a reduction instrument or other instrument to grasp onto the outer receiver 24. The arms 60 also include two oppositely disposed through-holes 66 for receiving retaining pins 38. The base of the inner bore includes a circumferential well 68 configured to receive the distal end of the spring 32. The circumferential well 68 extends around the screw retainer-receiving location 56 and serves to retain the distal end of the spring 32 within the outer receiver 24. The outer receiver 24 may also include cutouts 69 formed in the outer surface near the distal end to provide the outer receiver 24 with a reduced outer profile or ramped surface for improved insertion of the implant.

Figure 8:
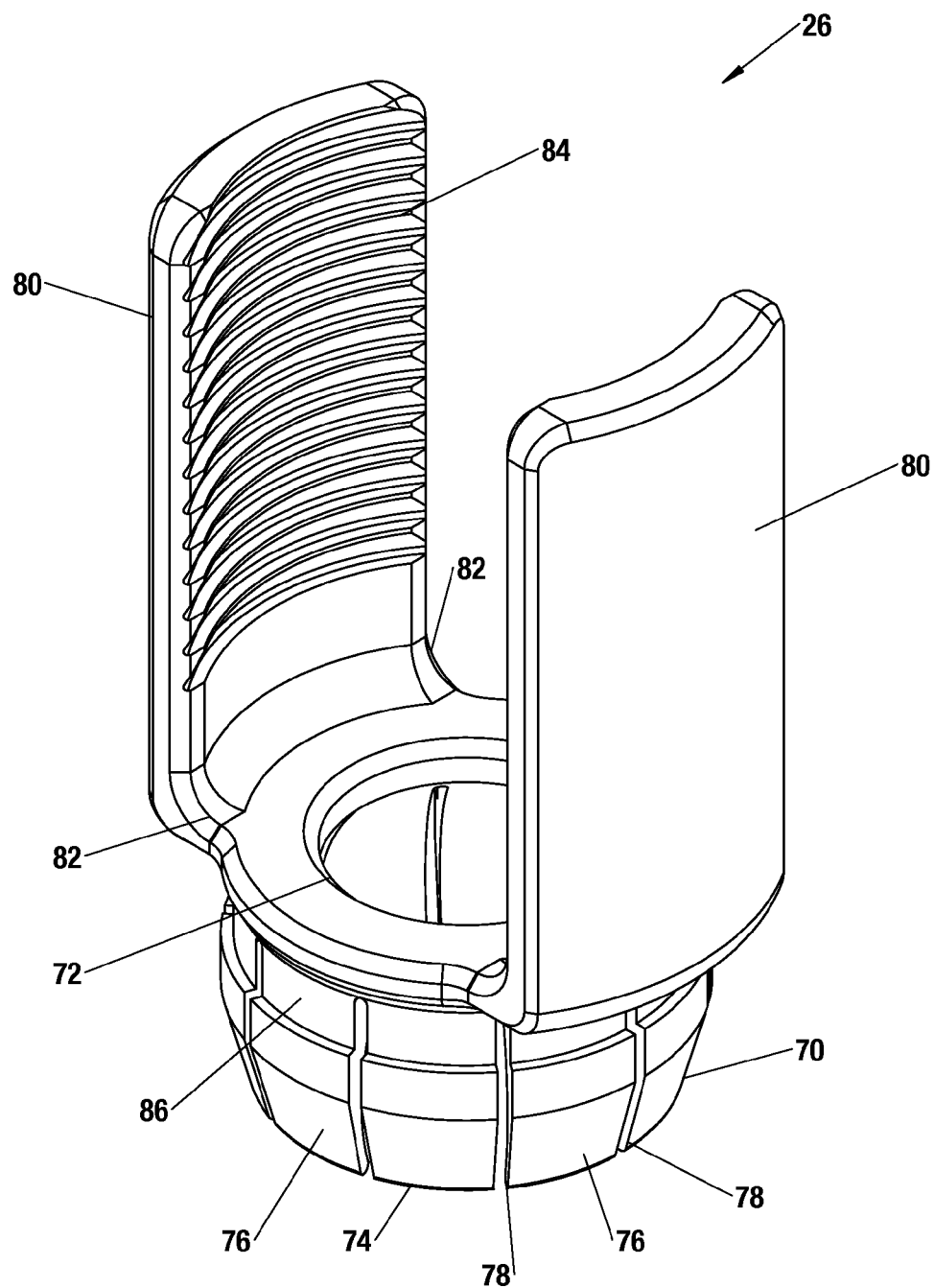
FIG. 8 is a top perspective view of a screw retainer according to the present invention.
Figure 9B:
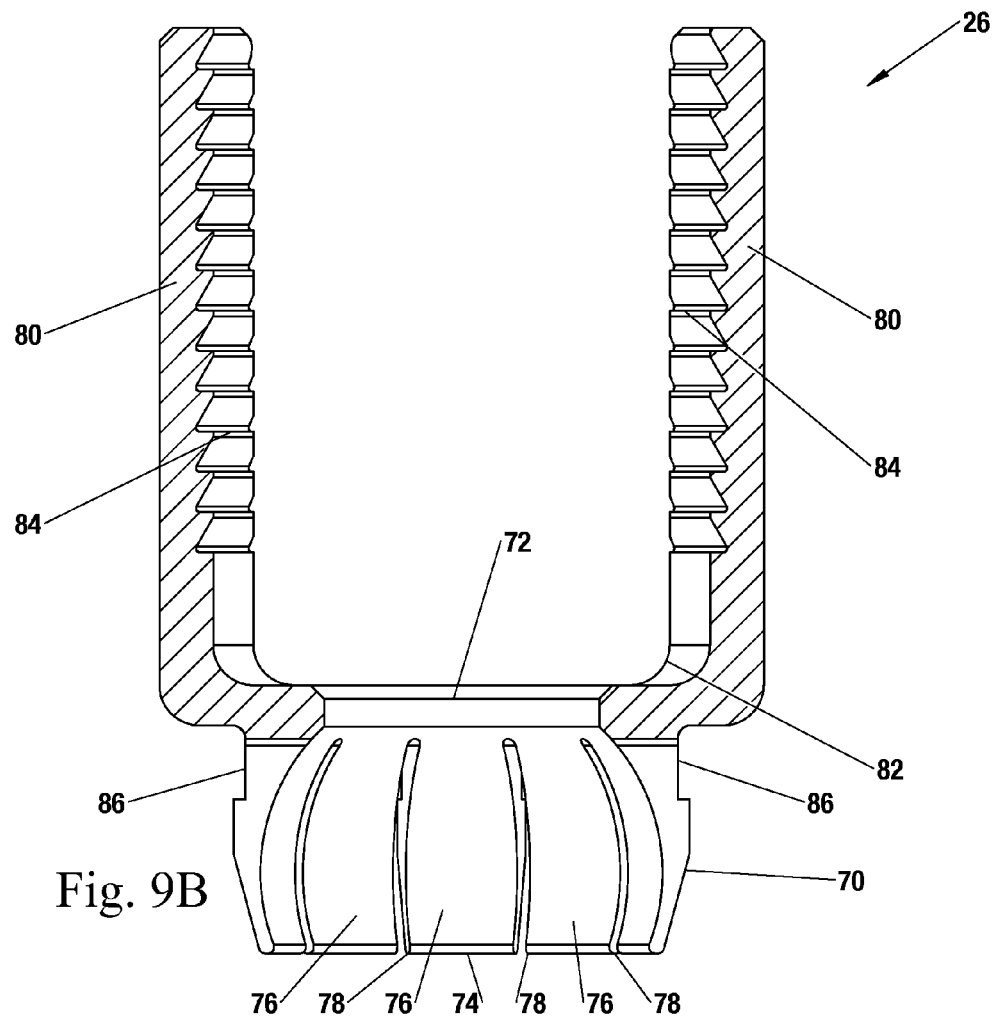
FIG. 9B is a cross-sectional view taken along line 9-9 of FIG. 9A of a screw retainer according to the present invention.
Figure 9A:
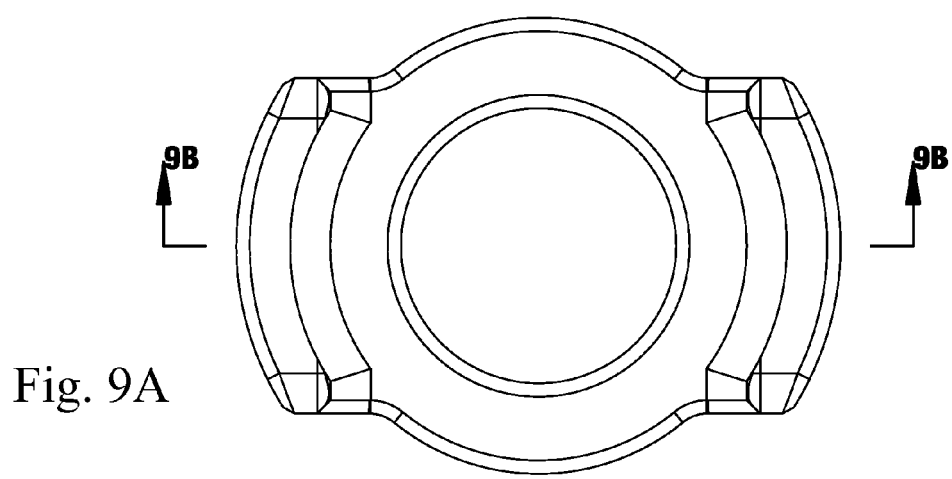
FIG. 9A is a top view of a screw retainer according to the present invention.

Turning now to FIGS. 8-9, there is shown a screw retainer 26. The distal end of the screw retainer 26 includes a cage 70 defining an interior that is configured to receive the bone screw head 42. The cage 70 includes a proximal opening 72 and a distal opening 74. The cage 70 includes a plurality of downwardly extending fingers 76 separated by slits 78 formed in the sidewall of the cage 70. The fingers 76 are capable of flexing slightly outwardly to accommodate the insertion of the bone screw head 42 into the interior of the cage 70. After the bone screw head 42 passes through the distal opening 74, the fingers 78 spread open and then spring back to their normal relaxed position to hold the bone screw head 42 inside the cage 70. The inner surface of the cage 70 is configured to conform to the size and shape of the bone screw head 42 such that when the bone fastener 22 is inserted into the cage 70, the bone fastener 22 may freely pivot and angulate polyaxially unimpededly relative to the screw retainer 26 as well as rotate about the longitudinal axis of the fastener 22. The outer surface of the cage 70 includes a circumferential notch 86 configured to receive and seat the retaining ring 28. The outer surface of the cage 70 also includes a ramped, tapered or angled distal end for easy insertion into and connection to the outer receiver 24.

Still referencing FIGS. 8-9, the screw retainer 26 further includes two upstanding, oppositely disposed arms 80. The arms 80 are curved circumferential segments that conform to the curved arms 62 of the outer receiver 24. The arms 80 are spaced apart from each other to define at least one channel 82 between the arms 80. In one variation, the channels 82 comprise two oppositely disposed, substantially U-shaped spaces that are substantially aligned with the channels 62 of the outer receiver 24. The channels 82 are shaped to receive an elongate fixation member 40 such as a spinal fixation rod or other elongate member. The channels 82 of the screw retainer 26 are substantially aligned with the channels 62 of the outer receiver 24. The inner surface of the arms 80 includes a plurality of teeth 84. The teeth 84 are configured to engage with the lock 34 as will be described in greater detail below.

Figure 10:
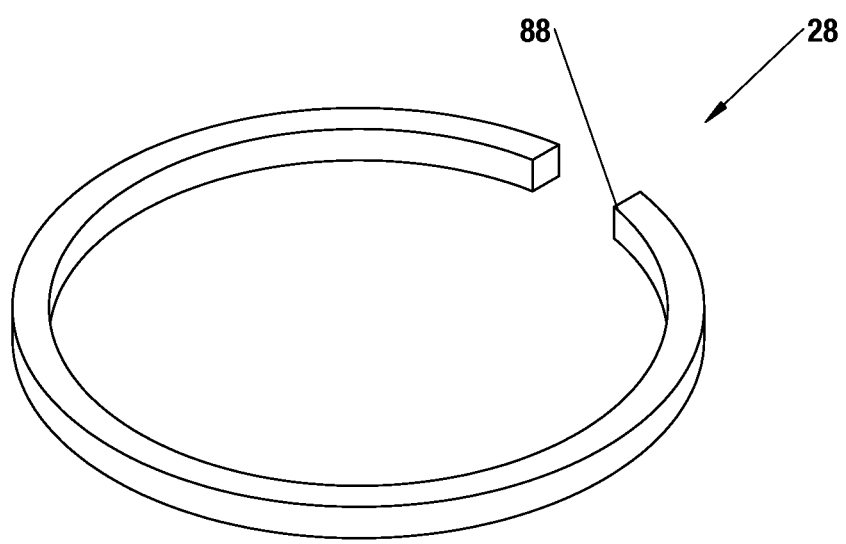
FIG. 10 is a top perspective view of a retaining ring according to the present invention.
Figure 11:
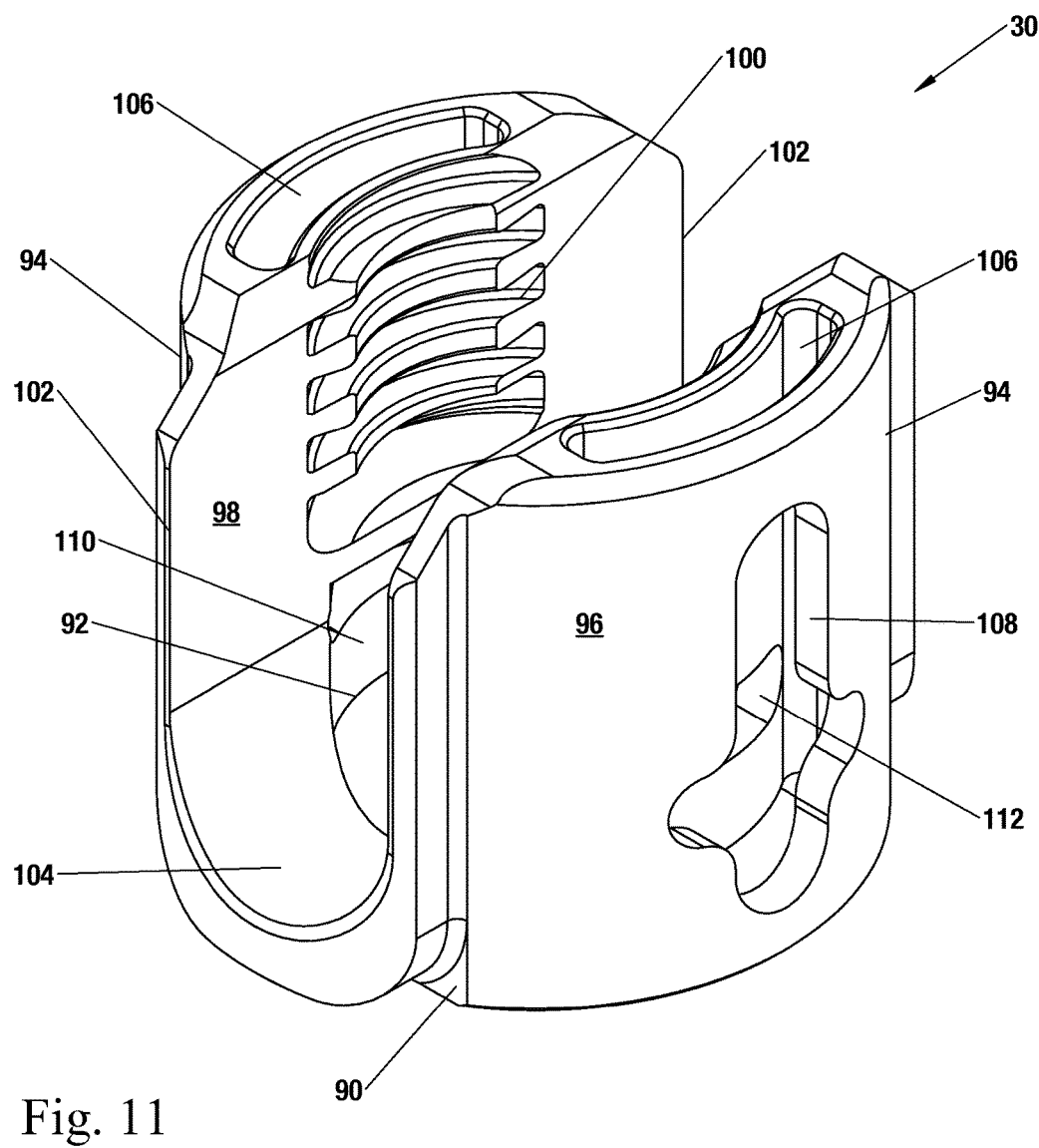
FIG. 11 is a top perspective view of an inner receiver according to the present invention.
Figure 12:
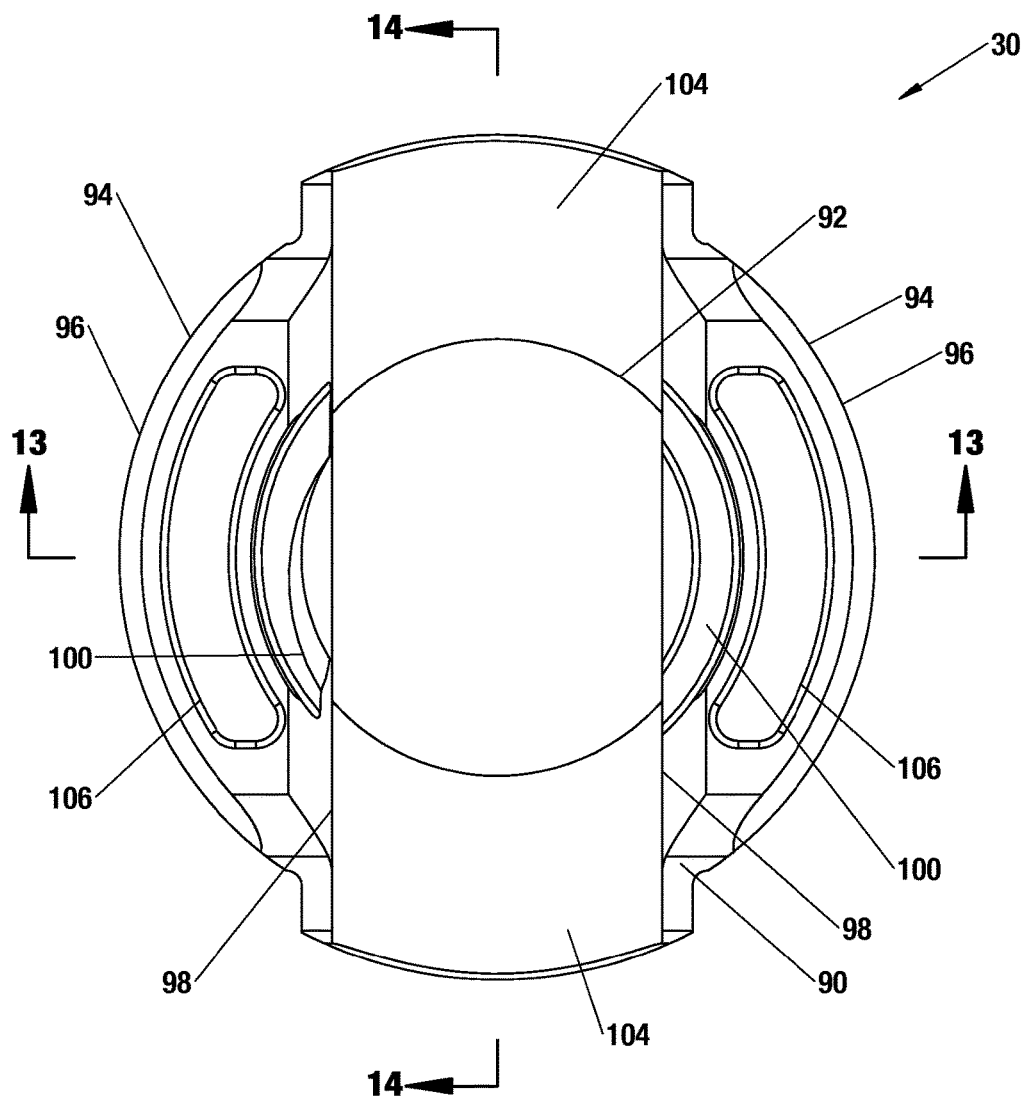
FIG. 12 is a top view of an inner receiver according to the present invention.
Figure 13:
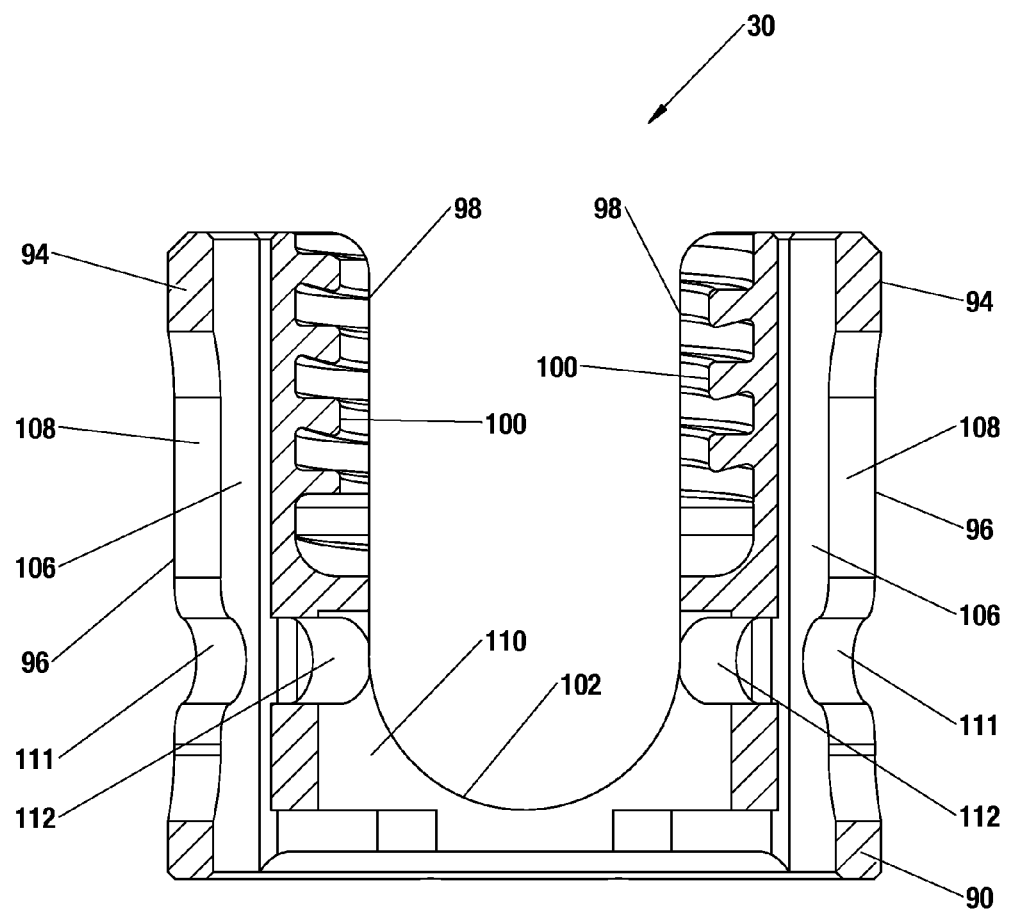
FIG. 13 is a cross-sectional view taken along line 13-13 of FIG. 12 of an inner receiver according to the present invention.
Figure 14:
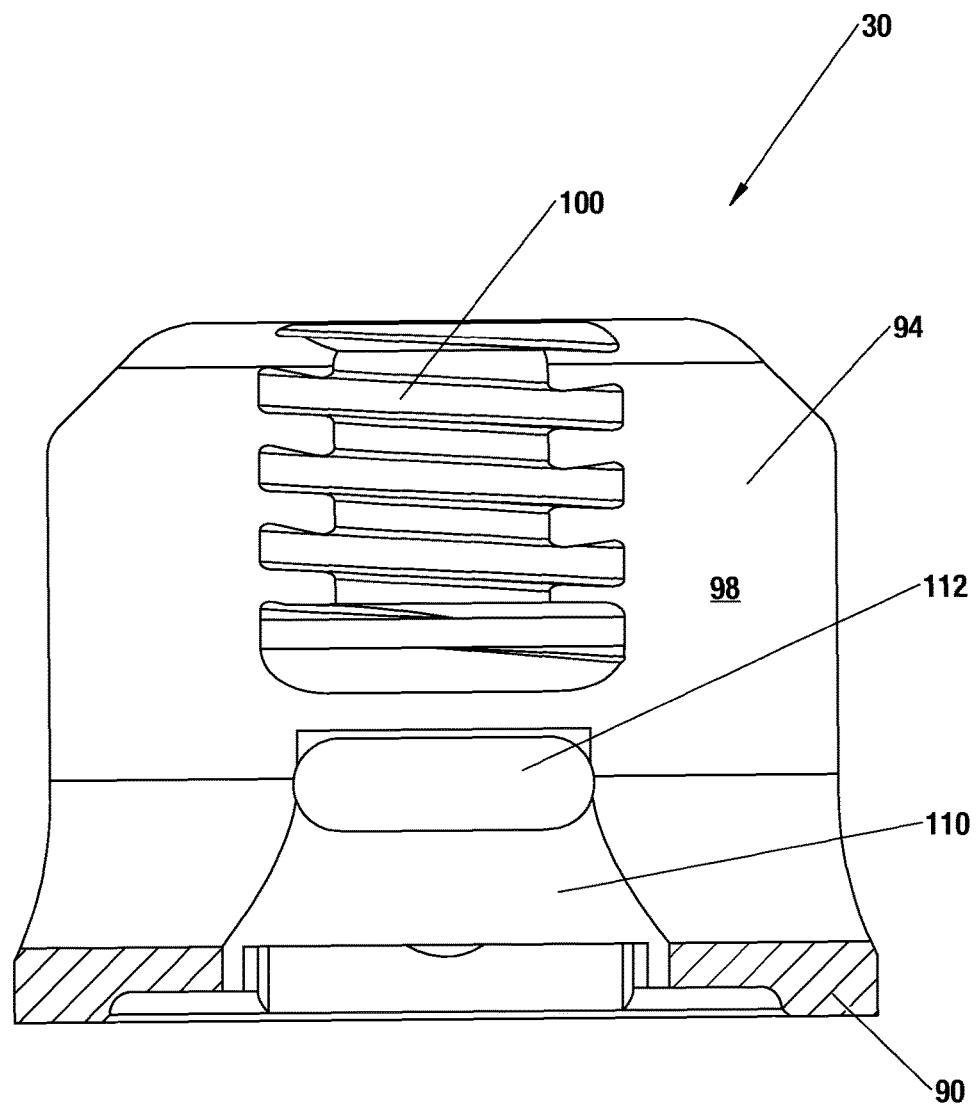
FIG. 14 is a cross-sectional view taken along line 14-14 of FIG. 12 of an inner receiver according to the present invention.

Turning to FIG. 10, the retaining ring 28 will now be described. The retaining ring 28 is substantially circular in shape and includes a cut 88 that forms a C-shaped ring. The C-ring includes spring-like properties such that the retaining ring 28 can flex into a reduced dimension and then spring back towards its normal relaxed configuration shown in FIG. 10. The retaining ring 28 is configured to fit inside the retaining ring slot 58 in the outer receiver 50. The retaining ring 28 is reduced in dimension and inserted into the screw retainer-receiving location 56 and snapped into the retaining ring slot 58 where the retaining ring 28 expands and remains. The bone fastener 22 is connected to the screw retainer 26 by inserting the bone screw head 42 into the distal opening 74 of the cage 70. The distal opening 74 of the cage 70 is slightly smaller than the lateral dimension of the bone screw head 42. When the bone screw head 42 is being inserted into the cage 70, the cage fingers 76 will flex outwardly to allow passage of the bone screw head 42 into the cage 70. The cage fingers 76 spring back behind the screw head 42. The bone screw head 42 snaps into the interior of the cage 70 and is retained therein being captured by the cage fingers 76. With the bone fastener 22 connected to the screw retainer 26 and the retaining ring 28 coupled to the outer receiver 24, the bone fastener 22 and screw retainer 26 combination is passed through into the distal opening 54 of the outer receiver 24 from the proximal direction until the angled distal end of the cage 70 ramps past the retaining ring 28 expanding it within the slot 58. The retaining ring 28 snaps into position in the circumferential notch 86 of the screw retainer 26. Thereby, the retaining ring 28 resides in both the circumferential notch 86 and the retaining ring slot 58 and connects the screw retainer 26 and bone fastener 22 to the outer receiver 24. The bone fastener 22 is permitted to angulate and rotate with respect to the outer receiver 24 when connected in an unlocked configuration to the outer receiver 24. Locking the angulation of the bone fastener 22 in a locked configuration will be described in greater detail below.

With reference to FIGS. 11-16, the inner receiver 30 will now be described in detail. The inner receiver 30 is substantially cylindrical in shape and sized and configured for insertion into the inner bore of the outer receiver 24. The base 90 includes a central aperture 92. The inner receiver 30 includes two upstanding, oppositely disposed arms 94 extend longitudinally upwardly from the base 90. The arms 94 are curved circumferential segments, each having an outer surface 96 and an inner surface 98. The inner surface 98 includes threads 100 sized and configured to engage with threads on the set screw 36. Two oppositely disposed substantially U-shaped channels 102 are defined between the arms 94 for receiving an elongate fixation member 40 inside the channels 102. The U-shaped channels 102 align substantially with the U-shaped channels 82 of the screw retainer 26 and the U-shaped channels 62 of the outer receiver 24 to permit seating of an elongate fixation member 40. Each U-shaped channel 102 of the inner receiver 30 includes an outwardly extending seat 104. The seats 104 form a cradling surface for the elongate fixation member 40 and have a curved surface in one variation. The outwardly extending seats 104 will translate upwardly and downwardly within the channels 62 of the outer receiver 24 and protrude into the channels 82 of the screw retainer 26. Each of the arms 94 includes a passageway 106 having an opening in the top of each arm 94. The passageway 106 extends from the opening at the top along the length of the arm 94, through the base 90 to an opening in the base 90 at the distal end of the inner receiver 30. The passageways 106 are curved to match the curvature of the arms 94 and the curvature of the arms 80 of the screw retainer 26. The passageways 106 are sized and configured to receive the arms 80 of the screw retainer 26. The inner receiver 30 is placed over the screw retainer 26 such that the arms 80 of the screw retainer 26 align with the distal openings of the passageways 106 and then the arms 80 of the screw retainer 26 are inserted into the passageways 106 to couple the inner receiver 30 to the screw retainer 26 in a fashion permitting the inner receiver 30 to move upwardly and downwardly relative to and along the screw retainer 26. The inner receiver 30 is coupled to the outer receiver 24 via retaining pins 38 which will be described in greater detail below. In one variation, the passageways 106 only include distal openings and do not have proximal openings.

Figure 15:
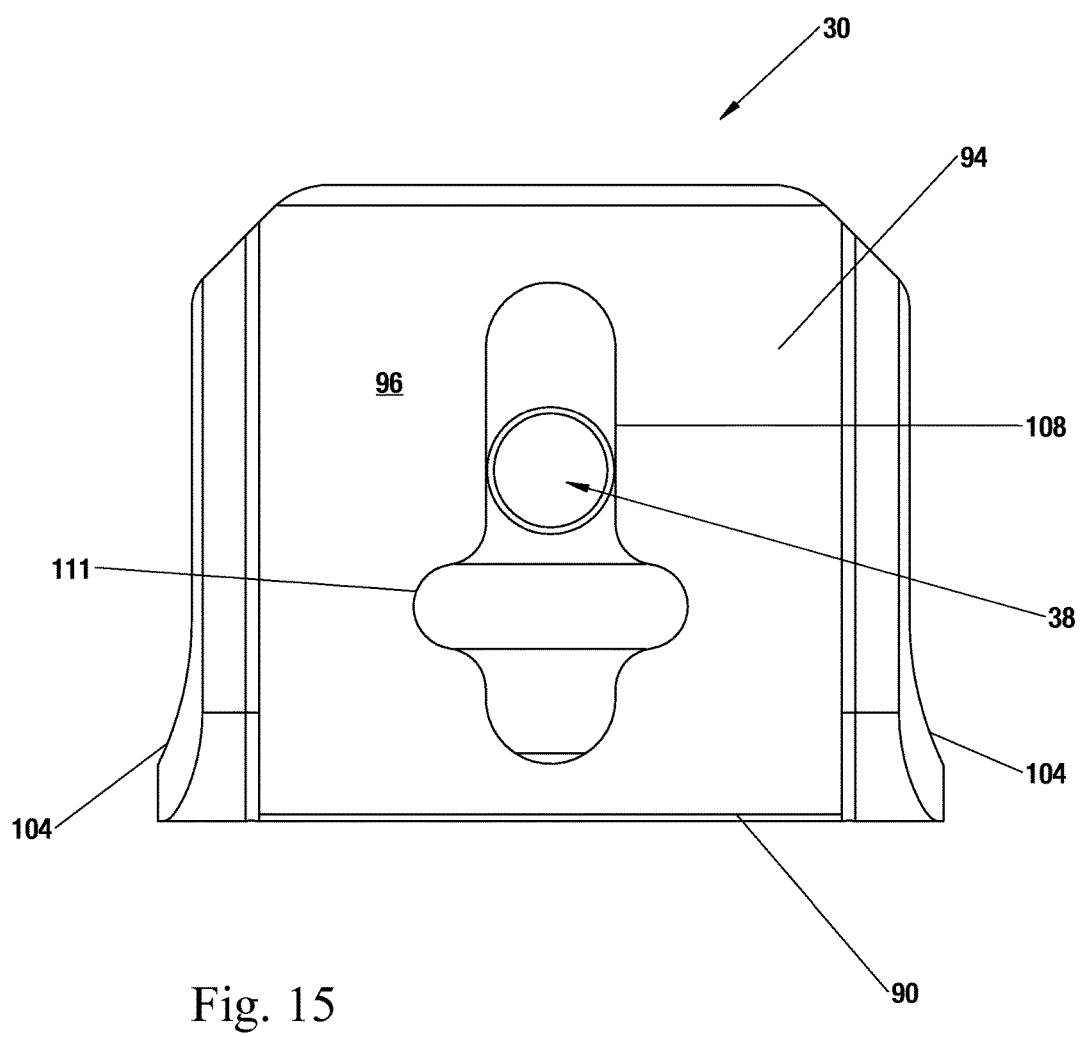
FIG. 15 is a side elevational view of an inner receiver and a retaining pin according to the present invention.
Figure 16:
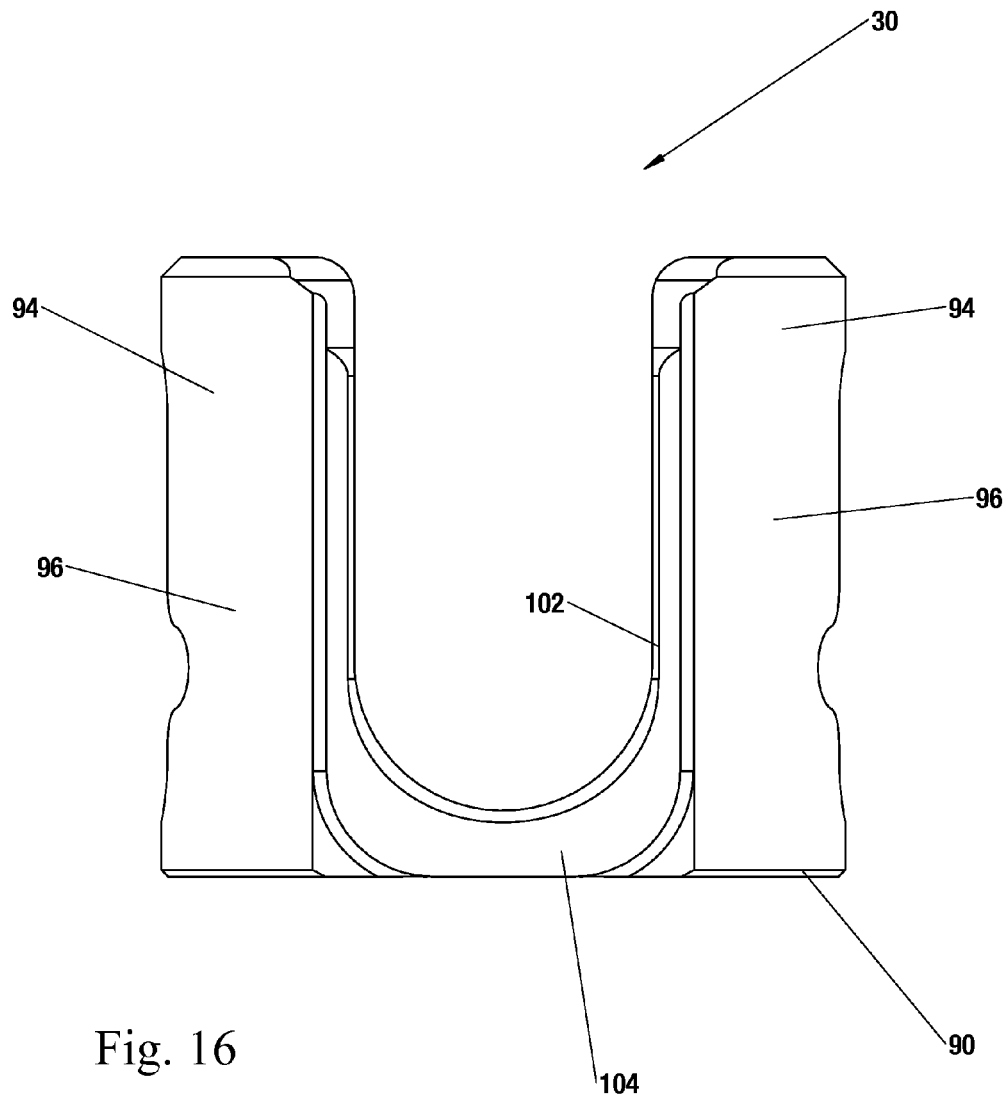
FIG. 16 is a side elevational view of an inner receiver according to the present invention.

Still referencing FIGS. 11-16, the inner receiver 30 includes a longitudinal notch 108 in the outer surface 96 of the arms 94. The longitudinal notches 108 are sized and configured to receive pins 38 that are passed through holes 66 in the outer receiver 24 and into the notches 108 to connect the inner receiver 30 to the outer receiver 24 such that the inner receiver 30 is permitted to translate upwardly and downwardly relative to the outer receiver 24 within the confines of the notches 108. FIG. 15 illustrates a pin 38 located within the notch 108. The proximal and distal ends of the notch 108 serve as proximal and distal stops, respectively, against which the pins 38 abut to limit translation of the inner receiver 30. In one variation, the notch 108 in each arm includes a laterally enlarged portion 111 that is located opposite the holes 112 so that locking prongs 130 of the lock 34 can be readily accessed with an instrument from outside the inner receiver 30.

Still referencing FIGS. 11-16, the interior of the inner receiver 30 includes a lock-receiving location 110. The lock-receiving location 110 is sized and configured to receive the lock 34 at the bottom of the inner receiver 30. The lock-receiving location 110 includes oppositely disposed holes 112 formed in the arms 94. Each hole 112 extends from the inner surface of the lock-receiving portion 110 into the adjacent passageway 106. The holes 112 are configured to receive the locking prongs 130 of the lock 34. The outer surfaces 96 of the arms 94 are configured for being received within the smooth inner surfaces of the outer receiver 24. The lock-receiving location 110 is configured to have a size and shape that corresponds to the outer perimeter size and shape of the lock 34 such that the lock 34 does not rotate relative to the inner receiver 30 when inside the lock receiving portion 110. The lock 34 is fixedly disposed inside the lock-receiving location 110 such that the lock 34 and the inner receiver 30 move together in relation to the screw retainer 26 and the outer receiver 24. In one variation, the lock 34 is integrally formed with the inner receiver 30 as one unit. In such a variation, the inner receiver 30 has locking prongs that are configured to engage the screw retainer 26.

Figure 17:
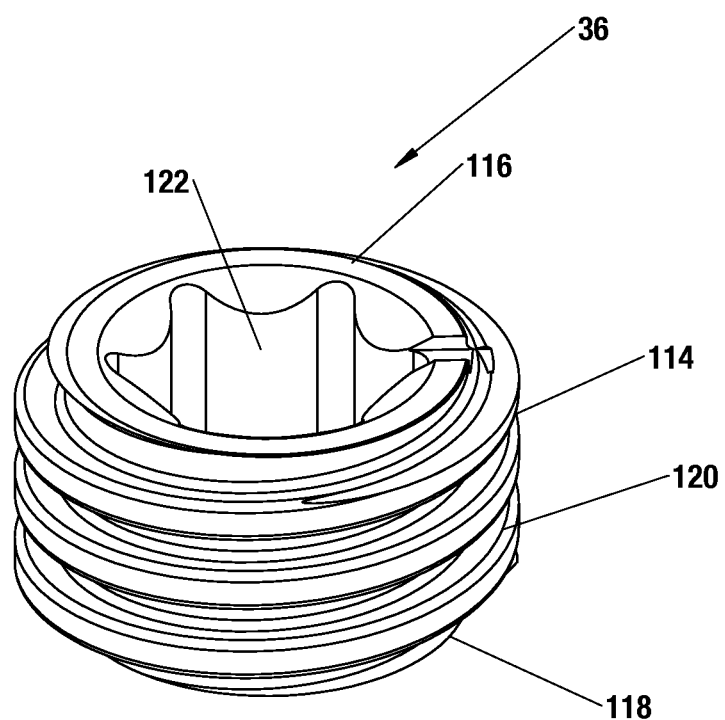
FIG. 17 is a top perspective view of a set screw according to the present invention.

Turning now to FIG. 17, the set screw 36 is a substantially cylindrical object having an outer surface 114 interconnected with a top surface 116 and a bottom surface 118. The outer surface 114 includes threads 120. The set screw 36 is configured to fit inside the inner receiver 30 and threadingly engage with the threads 100 on the inner surface 98 of the arms 94 of the inner receiver 30. The top surface 116 of the set screw 36 includes a driver receiving connection bore or socket 122 configured for engaging the tip of a driving instrument for turning the set screw 36 between a locked position and an unlocked position. Also, an indicator may be formed in the top surface 116 to facilitate alignment of the set screw threads with the threads of the inner receiver 30. The bottom surface 118 of the set screw 36 may include a conforming surface that conforms to the outer contour of an elongate fixation member 40. As the set screw 36 is threadingly translated downwardly into threaded engagement with the inner bore of the inner receiver 30 via threads 100, it will bear down with force onto the elongate fixation member 40 to lock it into the desired position in the z-axis vertical position of the inner receiver 30 relative to the outer receiver 24 and advantageously simultaneously lock the angulation of the bone fastener 22. This locking mechanism will be described in greater detail below. It is understood that threads may be substituted for any mechanical interlocking surface feature where suitable and appropriate.

With reference back to FIG. 2, the elongate fixation member 40 is a typical spinal fixation rod having a solid cylindrical shape having a circular cross-section and a length that spans any number of vertebrae that are desired to be fixed. A short portion of the elongate fixation member 40 is pictured in the figures for exemplary purposes.

With continued reference back to FIG. 2, a spring 32 is provided between the inner receiver 30 and the outer receiver 24. The spring 32 provides a bias force to raise the inner receiver 30 relative to the outer receiver 24 so that the z-axis position of the inner receiver 30 and hence, the z-axis position of the elongate fixation member 40 may be more easily adjusted. The distal end of the spring 32 is securely seated in the spring-receiving circumferential well 68 in the outer receiver 24. The proximal end of the spring 32 is configured to abut the base 90 of the inner receiver 30. Spring receiving areas may be provided on the inner receiver 30 to help retain the at least one spring 32 in position.

Figure 18:
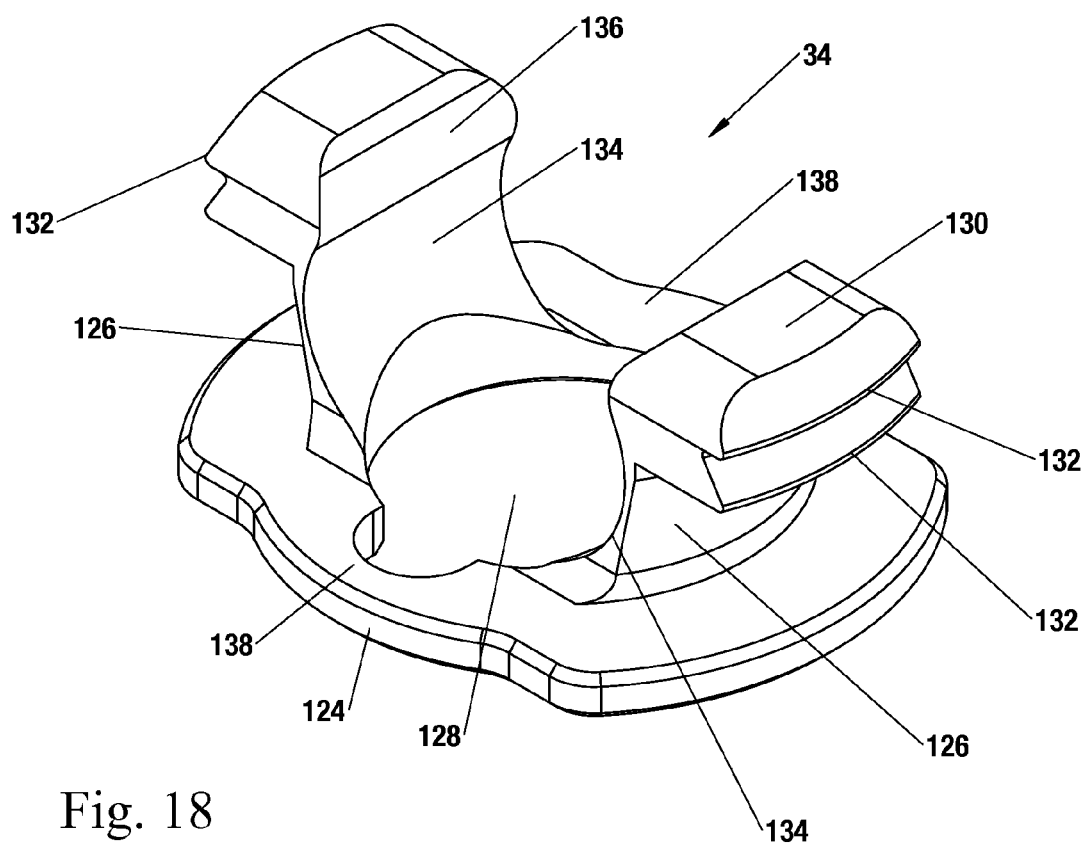
FIG. 18 is a top perspective view of a lock according to the present invention.
Figure 19:
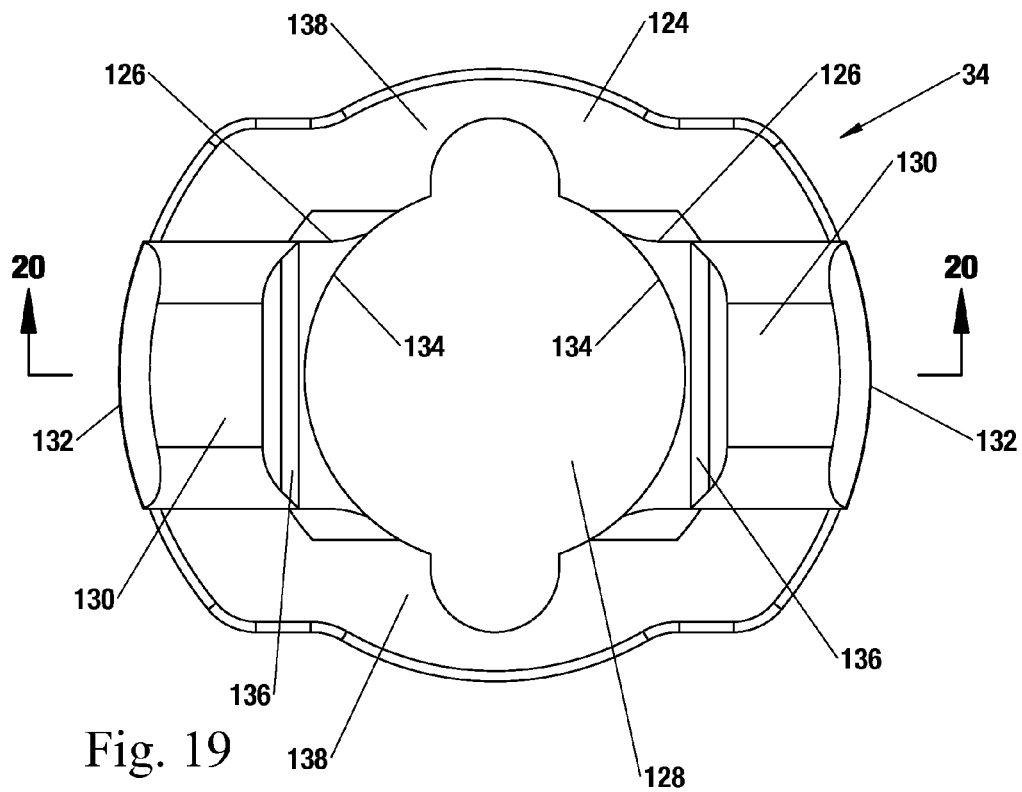
FIG. 19 is a top view of a lock according to the present invention.
Figure 20:
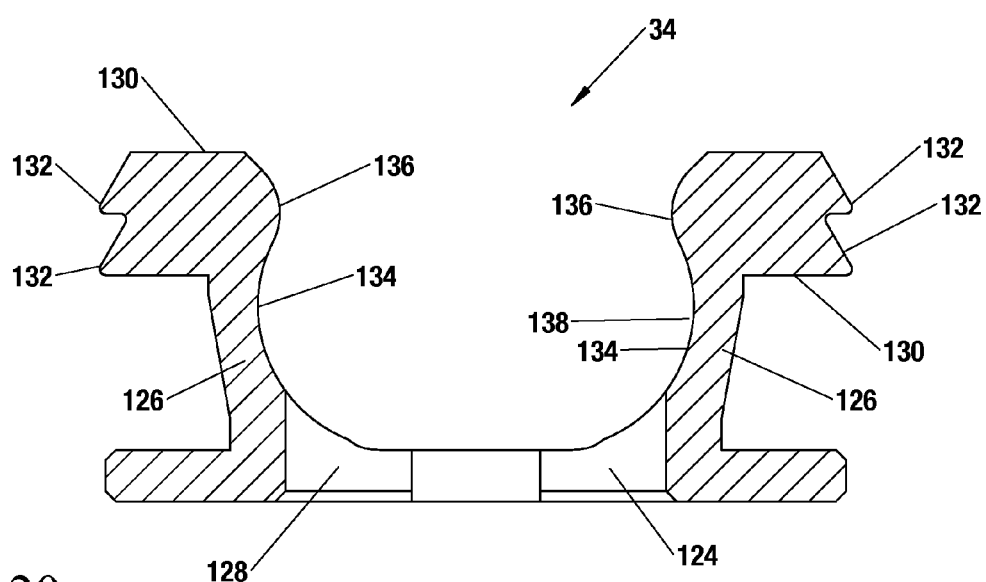
FIG. 20 is a cross-sectional view taken along line 20-20 of FIG. 19 of a lock according to the present invention.

Turning now to FIGS. 18-20, the lock 34 will now be described in detail. The lock 34 includes an annular base 124 with two upstanding, oppositely disposed arms 126 extending upwardly from the annular base 124. The arms 126 define two oppositely disposed and aligned channels 138. The base 124 includes a central aperture 128 and an outwardly extending flange that corresponds to the shape and size of the lock-receiving location 110 of the inner receiver 30 and is configured so that the lock 34 does not rotate with respect to the inner receiver 30. Each arm 126 includes a radially extending locking prong 130 that extends outwardly from the outer surface. The locking prongs 130 are oppositely located from and parallel to each other. The distal end of each prong 130 includes at least one tooth 132. Two teeth 132 on each locking prong 130 are depicted in FIG. 20. The locking prongs 130 are configured to extend through the holes 112 in the inner receiver 30 and the teeth 132 of the locking prongs 130 are configured to engage the teeth 84 on the screw retainer 26. The arms 126 of the lock 34 are configured to flex outwardly with respect to the annular base 124. When flexed outwardly, the arms 126 are biased to spring back to their normal relaxed position shown in FIGS. 18-20. In one variation, the arms 126 of the lock 34 flex outwardly and downwardly to engage the teeth 84 on the screw retainer 26 and simultaneously move the screw retainer 26 downwardly to lock the angulation of the bone fastener. The angulation of the arms has an outward force component and a downward force component which locks the vertical translation of the inner receiver relative to the outer receiver and the angulation of the bone fastener, respectively. The arms 126 include an inner surface 134. The inner surface 134 of the arms 126 have a shape or curvature that conforms to the shape and curvature of the outer surface of the elongate fixation member 40. The inner surface 134 of each arm 126 includes a bead 136 at the proximal end that forms a constriction or ramp. The beads 136 on the arms 126 extend inwardly toward the longitudinal axis to reduce the diametrical or lateral dimension between the arms 126. This dimension is smaller than the diameter or lateral dimension of an elongate fixation member 40 to be inserted and locked into the system 20. The beads 136 form a ramp for the elongate fixation member 40. When an elongate fixation member 40 is being inserted firstly, into the inner receiver 30 and, subsequently, secondly into the lock 34, the elongate fixation member 40 will contact the beads 136. Continued distal movement of the elongate fixation member 40 against the beads 136 will flex the arms 126 outwardly because of the reduced diametrical dimension at the beads 136. The arms 126 will flex outwardly such that the teeth 132 on the locking prongs 130 engage the teeth 84 of the screw retainer 26 to lock the vertical translation of the inner receiver 30 relative to the outer receiver 24 in a locked configuration that will be described in greater detail below. In essence, the elongate fixation member 40 has a first seating position inside the inner receiver and a second seating position that flexes the locking prongs of the lock.

The bone fixation system 20 is assembled by inserting the retaining ring 28 into the retaining ring slot 58 in the outer receiver 24. The retaining ring 26 may be reduced in dimension and inserted into the screw retainer-receiving location 56 and snapped into the retaining ring slot 58 where the retaining ring 26 expands and remains connected to the outer receiver 24. The bone fastener 22 is connected to the screw retainer 26 by inserting the bone screw head 42 into the distal opening 74 of the cage 70. The distal opening 74 of the cage 70 is slightly smaller than the lateral dimension of the bone screw head 42. When the bone screw head 42 is being inserted into the cage 70, the cage fingers 76 will flex outwardly to allow passage of the bone screw head 42 into the interior of the cage 70. The bone screw head 42 snaps into the interior of the cage 70 and is retained therein being captured by the cage fingers 76. With the bone fastener 22 connected to the screw retainer 26 and the retaining ring 28 coupled to the outer receiver 24, the bone fastener 22 and screw retainer 26 combination is passed through the distal opening 54 of the outer receiver 24 from the proximal direction until the angled distal end of the cage 70 ramps past the retaining ring 28 expanding it within the slot 58. The retaining ring 28 snaps into position in the circumferential notch 86 of the screw retainer 26. Thereby, the retaining ring 28 resides in both the circumferential notch 86 and the retaining ring slot 58 and connects the screw retainer 26 and bone fastener 22 to the outer receiver 24 such that the channels 62 of the outer receiver 24 are aligned with the channels 82 of the screw retainer 26. The bone fastener 22 is permitted to angulate and rotate with respect to the outer receiver 24 when connected and in an unlocked configuration. Next, the distal end of the spring 32 is placed into the well 68 such that the coils of the spring 32 encompass the screw retainer arms 80. The inner receiver 30 is located above the screw retainer arms 80 such that the arms 80 are aligned with the passageways 106 in the arms 94 of the inner receiver 90. The inner receiver 30 slides over the arms 80 of the screw retainer 26 and the distal end of the inner receiver 30 abuts the proximal end of the spring 32. The channels 102 of the inner receiver 30 are aligned with the channels 82 of the screw retainer 26 and with channels 62 of the outer receiver 24. The inner receiver 30 is pushed downwardly into the inner bore of the outer receiver 24 until part of the longitudinal notch 108 is aligned with the holes 66 in the outer receiver 24. The inner receiver 30 is held in place and retaining pins 38 are inserted into the holes 66 and into the longitudinal notch 108 thereby connecting the inner receiver 30 to the outer receiver 24 such that the inner receiver 30 is movable with respect to the outer receiver 24. The retaining pins 38 serve as stops when they contact the proximal or the distal ends of the longitudinal notches 108 limiting longitudinal travel and preventing the inner receiver 30 from disengaging with the outer receiver 24. The spring 32 biases the inner receiver 30 upwardly. The lock 34 is inserted into the lock-receiving location 110 of the inner receiver 30. The arms 126 of the lock 34 are compressed toward each other during insertion if necessary to place the lock 126 in position such that the locking prongs 130 extend through the holes 112 in the inner receiver 30. The locking prongs 130 snap into the holes 112 and the locking prongs 130 extend into the passageways 106. The passageways 106 are located inside the arms 94 and the locking prongs 130 extend through the holes 112 such that the teeth 132 of the lock 34 are in juxtaposition adjacent to the teeth 84 on the screw retainer 26 and in position to be activated into a locked configuration. The lock 34 translates together with the inner receiver 30. In one variation, the lock 34 is integral with the inner receiver 30 such that the inner receiver 30 includes locking prongs 130 that are configured to engage the screw retainer 26 when activated. The set screw 36 is inserted into the inner receiver 30 and threaded thereto. If an elongate fixation member 40 is used, the elongate fixation member 40 is inserted into the inner receiver 30 such that the elongate fixation member 40 extends through the channels 138 of the lock 34, through the channels 102 of the inner receiver 30, through the channels 82 of the screw retainer 26 and through the channels 62 of the outer receiver 24 and the set screw 36 is threaded above the elongate fixation member 40.

Figure 21B:
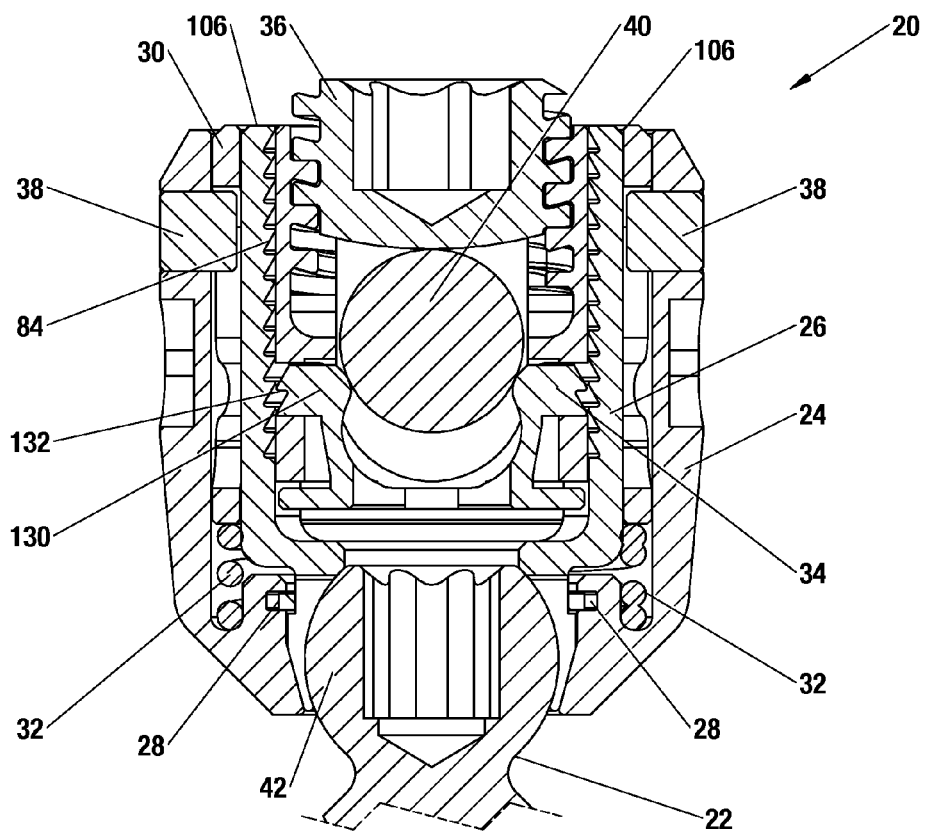
FIG. 21B is a cross-sectional view taken along line 21-21 of FIG. 21A of a bone fixation system in an unlocked, low-profile configuration according to the present invention.
Figure 21B:
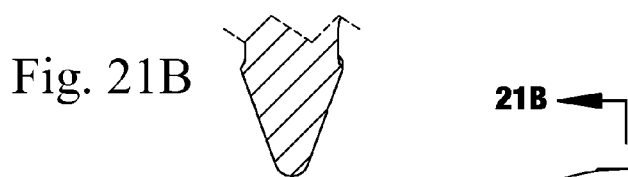
Figure 21A:
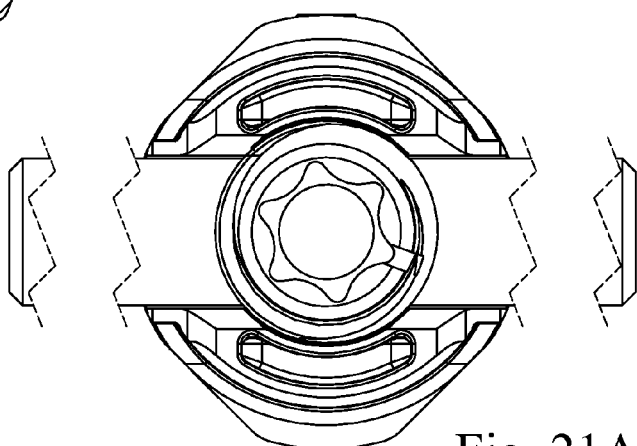
FIG. 21A is a top view of a bone fixation system in an unlocked, low profile configuration according to the present invention.
Figure 25:
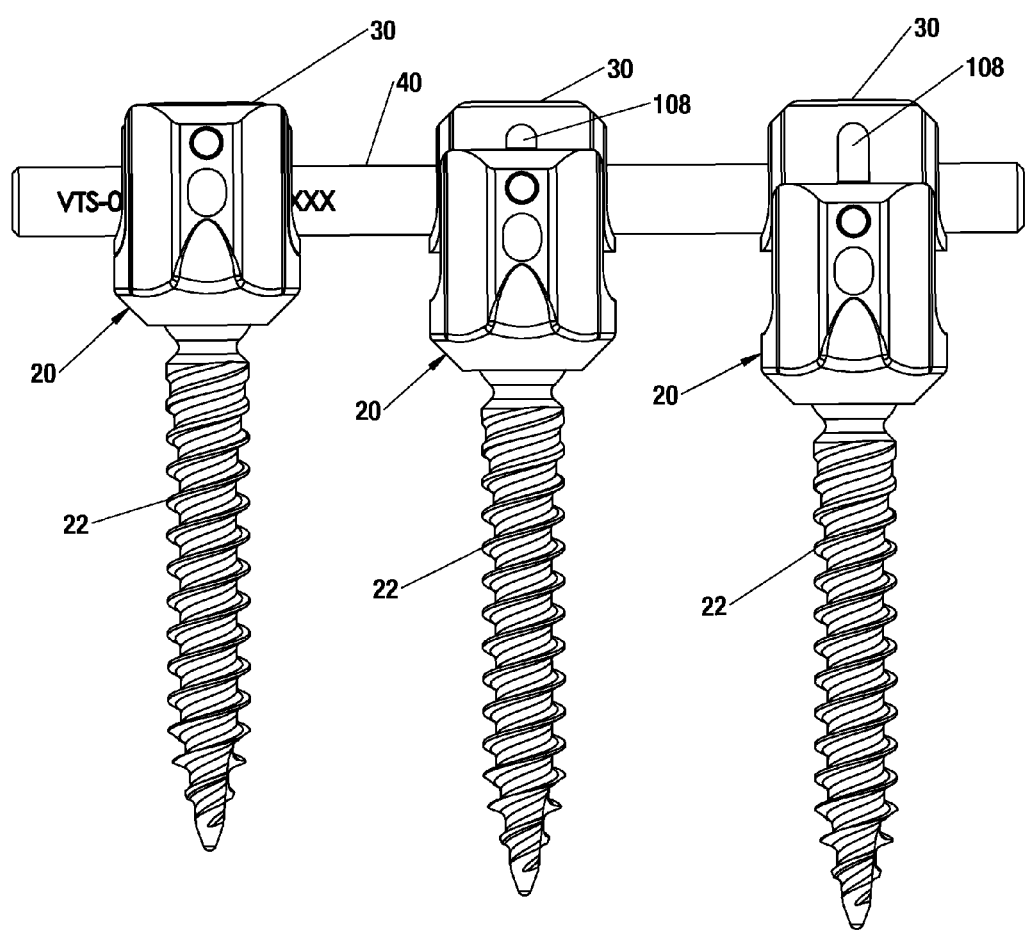
FIG. 25 is a side elevational view of three bone fixation systems locked to one elongate fixation member at variable heights according to the present invention.

In use, the bone fixation system 20 is provided with the elongate fixation member 40 and set screw 36 removed. The target implantation site is ascertained and the distal end of the bone fastener 22 is positioned at the target site. An insertion instrument having oppositely disposed prongs is employed to grasp the bone fixation system 20 by inserting the prongs of the insertion instrument into recesses 64 of the outer receiver 24. A bone screw driver is inserted into the inner bore of the inner receiver 30 and through the central aperture 128 of the lock 34, through the central aperture 92 of the inner receiver 30, through the distal opening 74 of the screw retainer 26, and through the distal opening 54 of the outer receiver 24 to engage with the driver connection feature 48 of the bone fastener 22. The bone fastener 22 is rotated and inserted into the target site and the driver is removed. One or more additional bone fixation systems 20 are implanted in the same or adjacent bone structures or vertebrae. An elongate fixation member 40 is inserted into the inner receiver 30 and the vertical longitudinal height of the inner receiver 30 is adjusted relative to the outer receiver 24 and relative to any one or more adjacent bone fixation systems 20 according to surgeon preference. The spring 32 biases the inner receiver 30 proximally upwardly facilitating the adjustment along the longitudinal axis by the surgeon. The set screw 36 may be inserted into the inner receiver 30 and threaded with the threads 100 of the inner receiver 30 during the height adjustment of the rod 30 to help contain the elongate fixation member 40. The inner receiver 30 together with the seated elongate fixation member 40 moves longitudinally relative to the outer receiver 24 when in an unlocked configuration. The cross-section of the bone fixation system 20 when in an unlocked configuration and in a low-profile position is shown in FIGS. 21A and 21B. In the unlocked configuration, the teeth 132 of the lock 34 do not engage the teeth 84 on the screw retainer 26. The bottom of the set screw 36 is shown in contact with the elongate fixation member 40 but the elongate fixation member 40 is not moved distally all the way into the lock 34 to deflect the locking prongs 130 outwardly into a locked configuration when in a first position. In the unlocked configuration shown in FIGS. 21A and 21B, the bone fastener 22 is permitted to rotate and angulate polyaxially with respect to the outer receiver 24 and the elongate fixation member 40 is permitted to move longitudinally with respect to the outer receiver 24. Also, in the unlocked position, the elongate fixation member 40 is allowed to move perpendicularly in a direction into and out of the page in FIGS. 21A and 21B. The low-profile position of the elongate fixation member 40 of the bone fixation system 20 is shown in a locked configuration in FIGS. 22A and 22B wherein the teeth 132 of the locking prongs 130 are engaged with the teeth 84 of the screw retainer 26. The locked configuration is achieved by advancing the set screw 36 further distally from the position shown in FIG. 21B into a second position such that the elongate fixation member 40 contacts the beads 136 of the lock 34 and deflects the locking prongs 130 outwardly such that the teeth 132 of the locking prongs 130 engage the teeth 84 on the screw retainer 26 as shown in FIG. 22B. The engagement of the teeth 84, 132 is configured such that contact with the locking prongs 130 results in the screw retainer 26 moving distally downwardly such that the cage 70 of the screw retainer 26 bears down onto the screw head 42 to advantageously lock the position of the bone fastener 22 relative to the outer receiver 24 and simultaneously lock the longitudinal position or height along the Z-axis of the elongate fixation member 40 and the inner receiver 30 relative to the outer receiver 24. The lock may operate first to lock the longitudinal translation of rod and then, secondly, lock the angulation of the bone fastener 22. FIGS. 23A and 23B illustrate a locked configuration in which the elongate fixation member 40 and inner receiver 30 are locked at an intermediate profile longitudinal position and FIGS. 24A and 24B illustrate a high-profile locked configuration in which the elongate fixation member 40 and inner receiver 30 are locked in an uppermost position along the Z-axis. In the intermediate profile position and in the high-profile position, the inner receiver 30 extends and protrudes above the proximal end of the outer receiver 24. FIG. 25 illustrates three bone fixation systems 20 according to the present invention locked to a single elongate fixation member 40 illustrating the variation heights. The bone fixation system 20 on the left is locked at a low-profile position, the bone fixation system 20 in the middle is locked at an intermediate position along the Z-axis, and the bone fixation system 20 on the right is locked at a high-profile or uppermost position along the longitudinal axis. The maximum range of travel of the inner receiver 30 and the elongate fixation member 40 relative to the outer receiver 24 is approximately 0.30 inches or approximately 5-10 millimeters. The ability to variably lock the height of the elongate fixation member 40 according to surgeon preference is provided by the bone fixation system 20 of the present invention. The set screw 36 may be withdrawn slightly to unlock the bone fixation system 20 so that the position along the longitudinal axis of elongate fixation member 40 can be adjusted as needed. The system 20 can be locked and unlocked to position and reposition the height for custom implantation. Hence, the bone fixation system of the present invention is highly versatile suiting all the needs of the surgeon in complex spinal surgeries.

It will be understood that many modifications can be made to the various disclosed embodiments without departing from the spirit and scope of the concept. For example, various sizes of the surgical devices are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention.

We claim:

1. A bone fixation system, comprising:
a bone fastener including:
a bone engaging portion; and
a head connected to the bone engaging portion;
an outer receiver having a proximal end, a distal end and a longitudinal axis; the outer receiver including:
a sidewall extending between the proximal end and the distal end and having an inner surface and an outer surface;
an inner bore extending between a top opening at the proximal end and a bottom opening at the distal end;
two oppositely disposed arms defined by the sidewall and at least one rod channel defined between the two arms; the at least one rod channel being interconnected with the top opening and the inner bore; a hole formed in each arm extending from the inner surface to the outer surface;
a screw retainer sized to fit inside the outer receiver; the screw retainer including two oppositely disposed arms connected to a bone fastener receiving portion at a distal end; the screw retainer including at least one channel defined between the arms; each arm has an interlocking inner surface; the bone fastener being coupled to the screw retainer in the bone fastener receiving portion such that the bone faster is permitted to angulate in an unlocked configuration;
an inner receiver sized to fit inside the outer receiver; the inner receiver including a base and two oppositely disposed arms extending upwardly from the base; the inner receiver includes at least one channel defined between the arms; each arm has an interlocking inner surface; each arm including a passageway having an opening at a proximal end of the inner receiver and extending to an opening at a distal end of the inner receiver; each passageway is sized and configured to receive an arm of the screw retainer within the passageway; the base of the inner receiver includes a lock-receiving portion having two oppositely disposed holes extending from an inside of the inner receiver outwardly into the passageways; the inner receiver being coupled to the outer receiver such that the inner receiver is movable longitudinally relative to the outer receiver;
a lock located inside the lock-receiving portion of the inner receiver; the lock including a rod-receiving location having reduced entryway; the rod receiving location being sized and configured to receive a connecting rod; the lock includes two outwardly extending locking prongs having distal interlocking surfaces; the locking prongs being configured to extend into the holes in the inner receiver such that the distal interlocking surfaces of the locking prongs engage the interlocking inner surfaces of the screw retainer in a locked configuration;
a set screw located between the arms of the inner receiver and having an interlocking outer surface configured to interlock with the interlocking inner surface of the arms of the inner receiver;
an elongate connecting rod located between the channels of the inner receiver;
wherein the bone fixation system includes an unlocked position in which the bone fastener angulates with respect to the outer receiver and the inner receiver is free to translate longitudinally with respect to the outer receiver; and a locked position in which the bone fastener and inner receiver are fixed with respect to the outer receiver.

2. The bone fixation system of claim 1 wherein the locked configuration is achieved by threading the set screw downwardly within the inner receiver to move the connecting rod into the rod receiving location which causes the locking prongs to extend outwardly to engage the screw retainer.

3. The bone fixation system of claim 1 wherein the screw retainer is configured to move downwardly onto the bone fastener when engaged by the locking prongs to lock the angulation of the bone fastener relative to the outer receiver.

4. The bone fixation system of claim 1 wherein the locking prongs extend outwardly to engage the inner interlocking surface of the screw retainer and simultaneously move the screw retainer downwardly onto the bone fastener to lock the angulation of the bone fastener relative to the outer receiver.

5. The bone fixation system of claim 1 wherein the locking prongs are configured to flex outwardly and downwardly when the connecting rod is moved into the rod receiving location to engage and move the screw retainer downwardly to lock the angulation of the bone fastener relative to the outer receiver.

6. The bone fixation system of claim 1 further including a spring disposed between the inner receiver and the outer receiver; the spring being configured to bias the inner receiver proximally relative to the outer receiver.

7. A bone fixation system, comprising:
a bone fastener;
an outer receiver; the bone fastener being coupled to the outer receiver and permitted to angulate with respect to the outer receiver in an unlocked configuration; the outer receiver defining an outer rod channel;
an inner receiver defining an inner rod channel; the inner receiver being nested within the outer receiver such that the inner rod channel is aligned with the outer rod channel;
a connecting rod removably insertable into the inner rod channel; the inner receiver being configured to translate in a longitudinal direction with an inserted connecting rod relative to the outer receiver in the unlocked configuration; and
a lock located inside the inner receiver and coupled to the inner receiver; the lock being configured to receive the connecting rod in a first position and in a second position; the second position being distal to the first position;
wherein the translation of the connecting rod and inner receiver is arrested and the angulation of the bone fastener is fixed when in a locked configuration; and
wherein the system transitions from an unlocked configuration to a locked configuration when the connecting rod is moved from the first position to the second position inside the lock.

8. The bone fixation system of claim 7 wherein the connecting rod is removably connectable to the inner receiver with a set screw inserted into the inner receiver.

9. The bone fixation system of claim 7 further including a set screw configured to be inserted into the inner receiver; and
wherein distal translation of the set screw moves the connecting rod from the first position into the second position.

10. The bone fixation system of claim 7 further including a screw retainer located inside the outer receiver and coupled to the bone fastener and to the outer receiver; the screw retainer includes interlocking inner surfaces; the lock includes outwardly extending locking prongs that engage the interlocking surfaces of the screw retainer to fix translation of the inner receiver relative to the outer receiver in the locked configuration.

11. The bone fixation system of claim 10 wherein the screw retainer translates downwardly from the unlocked configuration to a locked configuration to lock the angulation of the bone fastener.

12. The bone fixation system of claim 10 wherein the screw retainer includes a retainer rod channel; the screw retainer being nested inside the outer receiver such that the retainer rod channel is aligned with the outer rod channel and the inner rod channel.

13. The bone fixation system of claim 10 wherein the screw retainer includes oppositely disposed arms and the inner receiver includes longitudinal passageways configured to receive the arms of the screw retainer; the inner receiver translating with respect to the screw retainer in the unlocked configuration.

14. The bone fixation system of claim 13 wherein an inner surface of the inner receiver includes holes configured to permit the locking prongs to extend through the holes to engage the arms of the screw retainer inside the passageways of the inner receiver.

15. The bone fixation system of claim 7 wherein the inner receiver includes a lock receiving portion and the lock is sized and configured such that the lock does not rotate relative to the inner receiver when inside the lock receiving portion.

16. A bone fixation system defining a longitudinal axis, comprising:
a bone fastener;
an outer receiver coupled to the bone fastener;
a screw retainer located inside the outer receiver, wherein the screw retainer includes two arms each having a threaded inner surface; the screw retainer being connected to the outer receiver and coupled to the bone fastener;
an inner receiver nested within the outer receiver; the inner receiver having an inner surface and an outer surface and configured to receive a connecting rod inside the inner receiver; the inner receiver having two passageways that are sized and configured to receive the two arms of the screw retainer therein such that the inner receiver is movable longitudinally along and relative to the screw retainer in an unlocked configuration.

17. The bone fixation system of claim 16 wherein the inner receiver has at least one hole extending from the inner surface into the passageway; and
a lock located inside the inner receiver and coupled to the inner receiver; the lock having locking prongs configured to extend through the at least one hole to engage the screw retainer to lock translation of the inner receiver relative to the outer receiver.

18. The bone fixation system of claim 16 wherein longitudinal translation of the inner receiver relative to the outer receiver is limited by a pin located between the inner receiver and the outer receiver moving inside a notch.

19. The bone fixation system of claim 16 further including a connecting rod removably insertable into the inner receiver; the connecting rod configured to translate with the inner receiver along the longitudinal axis in the unlocked configuration.

20. A bone fixation system defining a longitudinal axis, comprising:
a bone fastener;
an outer receiver coupled to the bone fastener;
a screw retainer located inside the outer receiver, the screw retainer being connected to the outer receiver and coupled to the bone fastener;
an inner receiver nested within the outer receiver; the inner receiver having an inner surface and an outer surface and configured to receive a connecting rod inside the inner receiver; the inner receiver having at least one passageway that is sized and configured to receive at least part of the screw retainer inside the at least one passageway such that the inner receiver is movable longitudinally along and relative to the screw retainer in an unlocked configuration; wherein the inner receiver has at least one hole extending from the inner surface into the passageway; and
a lock located inside the inner receiver and coupled to the inner receiver; the lock having locking prongs configured to extend through the at least one hole to engage the screw retainer to lock translation of the inner receiver relative to the outer receiver.

21. The bone fixation system of claim 20 wherein longitudinal translation of the inner receiver relative to the outer receiver is limited by a pin located between the inner receiver and the outer receiver moving inside a notch.

22. The bone fixation system of claim 20 further including a connecting rod removably insertable into the inner receiver; the connecting rod configured to translate with the inner receiver along the longitudinal axis in the unlocked configuration.

* * * * *